(12) United States Patent
Ikenaga et al.

(10) Patent No.: US 11,788,966 B2
(45) Date of Patent: Oct. 17, 2023

(54) IMAGING SYSTEM

(71) Applicant: Sony Group Corporation, Tokyo (JP)

(72) Inventors: Yuichiro Ikenaga, Kanagawa (JP); Satoshi Nagae, Tokyo (JP); Yuuichirou Kita, Aichi (JP)

(73) Assignee: SONY GROUP CORPORATION, Tokyo (JP)

(*) Notice: Subject to any disclaimer, the term of this patent is extended or adjusted under 35 U.S.C. 154(b) by 0 days.

(21) Appl. No.: 17/555,515

(22) Filed: Dec. 20, 2021

(65) Prior Publication Data
US 2022/0120689 A1    Apr. 21, 2022

Related U.S. Application Data

(63) Continuation of application No. 16/324,675, filed as application No. PCT/JP2017/024582 on Jul. 5, 2017, now Pat. No. 11,221,296.

(30) Foreign Application Priority Data

Aug. 19, 2016    (JP) .................................. 2016-161544

(51) Int. Cl.
| G01N 21/64 | (2006.01) |
| G02B 23/24 | (2006.01) |
| A61B 90/20 | (2016.01) |
| G02B 21/00 | (2006.01) |
| A61B 1/00 | (2006.01) |
| A61B 90/00 | (2016.01) |

(Continued)

(52) U.S. Cl.
CPC ........... G01N 21/6458 (2013.01); A61B 1/00 (2013.01); A61B 1/043 (2013.01); A61B 5/0071 (2013.01);
(Continued)

(58) Field of Classification Search
CPC ...... G01N 21/6458; G01N 21/64; A61B 1/00; A61B 1/043; A61B 5/0071; A61B 90/20;
(Continued)

(56) References Cited

U.S. PATENT DOCUMENTS

2002/0138008 A1    9/2002    Tsujita et al.
2004/0186351 A1    9/2004    Imaizumi et al.
(Continued)

FOREIGN PATENT DOCUMENTS

JP    8-224209 A    9/1996
JP    10-201707 A    8/1998
(Continued)

OTHER PUBLICATIONS

International Search Report dated Sep. 26, 2017 in PCT/JP2017/024582, 2 pages.
(Continued)

*Primary Examiner* — Peter Luong
(74) *Attorney, Agent, or Firm* — XSENSUS LLP

(57) ABSTRACT

An imaging system includes a light source emitting light at least a first excitation wavelength band to excite a first fluorescence material emitting a first fluorescence in a near-infrared wavelength band and light a second excitation wavelength band to excite a second fluorescence material emitting a second fluorescence in a visible wavelength band, a first image sensor receiving light including the first fluorescence and outputs a first imaging signal, a second image sensor receives light including the second fluorescence and output a second imaging signal, an optical element that separates the first fluorescence into a first optical branch and the second fluorescence into a second optical branch; and a pass filter in the first optical branch transmitting light having a near-infrared wavelength band and block light having a wavelength equal to or less than a predetermined wavelength belonging the visible wavelength band.

20 Claims, 14 Drawing Sheets

(51) Int. Cl.
*A61B 1/04* (2006.01)
*A61B 5/00* (2006.01)

(52) U.S. Cl.
CPC ............ *A61B 90/20* (2016.02); *A61B 90/361* (2016.02); *A61B 90/37* (2016.02); *G01N 21/64* (2013.01); *G02B 21/00* (2013.01); *G02B 23/24* (2013.01)

(58) Field of Classification Search
CPC ...... A61B 90/361; A61B 90/37; G02B 21/00; G02B 23/24
See application file for complete search history.

(56) References Cited

U.S. PATENT DOCUMENTS

| | | | |
|---|---|---|---|
| 2005/0027166 A1 | 2/2005 | Matsumoto et al. | |
| 2005/0224692 A1* | 10/2005 | Tsuchiya | G02B 21/16 250/201.3 |
| 2010/0079587 A1 | 4/2010 | Yoshida | |
| 2015/0008340 A1 | 1/2015 | Fujita et al. | |
| 2017/0343477 A1* | 11/2017 | Santori | G01J 3/0224 |

FOREIGN PATENT DOCUMENTS

| | | |
|---|---|---|
| JP | 3962122 B2 | 8/2007 |
| JP | 2010-82040 A | 4/2010 |
| JP | 2012-88304 A | 5/2012 |
| JP | 2013-200209 A | 10/2013 |
| JP | 2013-248319 A | 12/2013 |
| JP | 2016-120105 A | 7/2016 |
| WO | 2016/117071 A1 | 7/2016 |

OTHER PUBLICATIONS

Office Action dated Mar. 24, 2020 in Japanese Patent Application No. 2016-161544, 9 pages.

* cited by examiner

IMAGING SYSTEM

CROSS-REFERENCE TO RELATED APPLICATIONS

This application is a continuation of U.S. application Ser. No. 16/324,675, filed Feb. 11, 2019, which is based on PCT filing PCT/JP2017/024582, filed Jul. 5, 2017, and claims priority to Japanese Application No. 2016-161544, filed Aug. 19, 2016, the entire contents of each are incorporated herein by reference.

TECHNICAL FIELD

The present disclosure relates to an imaging system.

BACKGROUND ART

With the development of surgical methods and surgical instruments, surgery (so-called, microsurgery) for performing various treatments while observing affected areas using medical observation apparatuses such as endoscopes and surgical microscopes has been frequently performed. In addition, such medical observation apparatuses are not limited to apparatuses capable of optically observing affected areas, and apparatuses and systems displaying images of affected areas picked up by image pickup apparatuses (cameras) or the like as electronic images on display apparatuses, such as monitors, have also been proposed.

Further, in recent years, an observation method using an observation apparatus such as an endoscope or a surgical microscope is not limited to only a method of observing a surgical field using light in a band of visible light, and various observation methods called special light observation such as narrow band imaging (NBI), auto fluorescence imaging (AFI), and infrared imaging (IRI) have been proposed.

For example, in auto fluorescence imaging, a fluorescent material having affinity for a lesion such as cancer is previously administered to an examination target person (patient), and excitation light for exciting the fluorescent material is emitted, so that a lesion portion is observed using a fluorescent image of fluorescence emitted from the fluorescent material accumulated in the lesion portion (that is, an observation image based on a result of detection of fluorescence). For example, Patent Literature 1 discloses an example of an endoscope apparatus capable of performing auto fluorescence imaging using indocyanine green (ICG) as a fluorescent material.

CITATION LIST

Patent Literature

Patent Literature 1: JP 3962122B

DISCLOSURE OF INVENTION

Technical Problem

Incidentally, in recent years, various fluorescent materials other than ICG have been proposed as fluorescent materials which are used for auto fluorescence imaging, and such fluorescent materials also include fluorescent materials emitting fluorescence having a wavelength band different from that of ICG For example, ICG emits fluorescence having a wavelength of approximately 820 nm (that is, light in a near-infrared band). On the other hand, fluorescent materials emitting fluorescence in a band of visible light such as fluorescein, 5-aminolevulinic acid (5ALA), and laserphyrin (registered trademark) have also been proposed.

Consequently, in the present disclosure, an imaging system is proposed which is capable of picking up a fluorescent image, corresponding to a fluorescent material to be used, in a more suitable mode even under a situation where a plurality of types of fluorescent materials is selectively used.

Solution to Problem

According to the present disclosure, there is provided an imaging system including: a light source apparatus which irradiates a predetermined image pickup target with light including a component in at least a portion of a wavelength band of an excitation wavelength of each of a plurality of types of fluorescent materials including a first fluorescent material emitting fluorescence belonging to a near-infrared wavelength band and a second fluorescent material emitting fluorescence belonging to a visible light wavelength band; and an image pickup apparatus which picks up an image acquired by a predetermined optical system unit. The image pickup apparatus includes a branching optical system that includes a dichroic film separating the light belonging to the visible light wavelength band and the light belonging to the near-infrared wavelength band from each other, a first image pickup element which is provided at a stage after the branching optical system and on which the light belonging to the near-infrared wavelength band which is separated by the dichroic film is imaged, and a second image pickup element which is provided at a stage after the branching optical system and on which at least a portion of the light belonging to the visible light wavelength band which is separated by the dichroic film is imaged, a fluorescent image of the fluorescence emitted from the first fluorescent material is picked up by the first image pickup element, and a fluorescent image of the fluorescence emitted from the second fluorescent material is picked up by the second image pickup element.

Advantageous Effects of Invention

As described above, according to the present disclosure, there is provided an imaging system capable of observing a fluorescent observation image, corresponding to a fluorescent material to be used, in a more suitable mode even under a situation where a plurality of fluorescent materials are selectively used.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
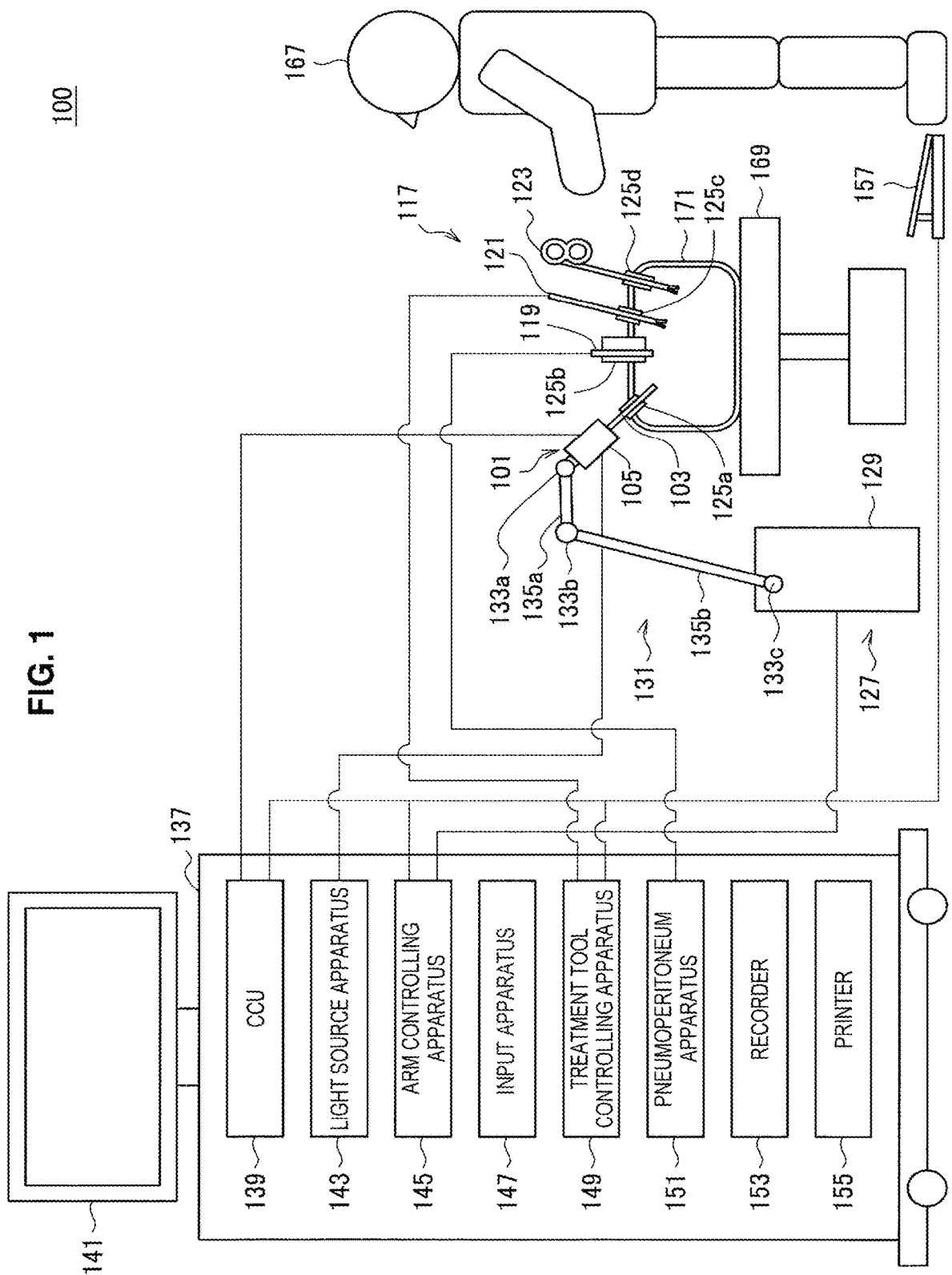
FIG. 1 is a view depicting an example of a schematic configuration of an endoscopic image pickup system according to an embodiment of the present disclosure.

Hereinafter, (a) preferred embodiment (s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that a description will be given in the following order.
1. Configuration of endoscopic image pickup system
2. Examination of auto fluorescence imaging
3. Technical features
3.1. Schematic configuration of camera head
3.2. Configuration example 1 of two-plate type camera head
3.3. Configuration example 2 of two-plate type camera head
3.4. Configuration example of three-plate type camera head
3.5. Operational effects
4. Example of hardware configuration of CCU
5. Application example
6. Conclusion

1. CONFIGURATION OF ENDOSCOPIC IMAGE PICKUP SYSTEM

Figure 2:
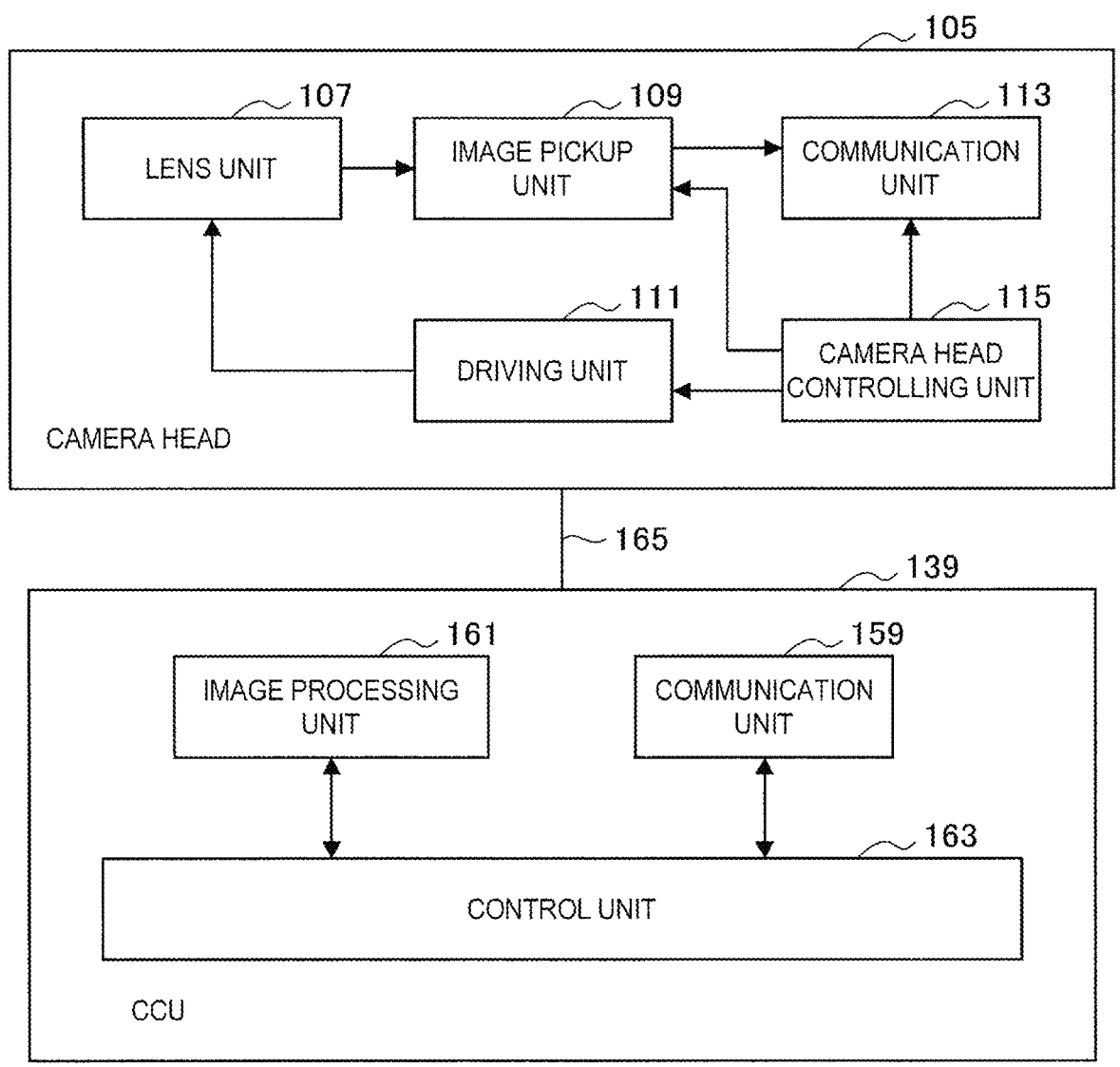
FIG. 2 is a block diagram depicting an example of a functional configuration of a camera head and a camera control unit (CCU) depicted in FIG. 1.

First, with reference to FIGS. 1 and 2, an example of a schematic configuration of an endoscopic image pickup system according to an embodiment of the present disclosure is described. For example, FIG. 1 is a view depicting an example of a schematic configuration of an endoscopic image pickup system to which the technology according to an embodiment of the present disclosure can be applied, and it illustrates an example in a case where the endoscopic image pickup system includes a so-called endoscopic surgery system. In FIG. 1, a state is depicted in which a surgeon (medical doctor) 167 is using the endoscopic surgery system 100 to perform surgery for a patient 171 on a patient bed 169. As depicted, the endoscopic surgery system 100 includes an endoscope 101, other surgical tools 117, a supporting arm apparatus 127 which supports the endoscope 101 thereon, and a cart 137 on which various apparatuses for endoscopic surgery are mounted.

In endoscopic surgery, in place of incision of the abdominal wall to perform laparotomy, a plurality of tubular aperture devices called trocars 125a to 125d is used to puncture the abdominal wall. Then, a lens barrel 103 of the endoscope 101 and the other surgical tools 117 are inserted into body cavity of the patient 171 through the trocars 125a to 125d. In the example depicted, as the other surgical tools 117, a pneumoperitoneum tube 119, an energy device 121 and forceps 123 are inserted into body cavity of the patient 171. Further, the energy device 121 is a treatment tool for performing incision and peeling of a tissue, sealing of a blood vessel or the like by high frequency current or ultrasonic vibration. However, the surgical tools 117 depicted are mere examples at all, and as the surgical tools 117, various surgical tools which are generally used in endoscopic surgery such as, for example, tweezers or a retractor may be used.

An image of a surgical region in a body cavity of the patient 171 picked up by the endoscope 101 is displayed on a display apparatus 141. The surgeon 167 would use the energy device 121 or the forceps 123 while watching the image of the surgical region displayed on the display apparatus 141 on the real time basis to perform such treatment as, for example, resection of an affected area. It is to be noted that, though not depicted, the pneumoperitoneum tube 119, the energy device 121 and the forceps 123 are supported by the surgeon 167, an assistant or the like during surgery.

(Supporting Arm Apparatus)

The supporting arm apparatus 127 includes an arm unit 131 extending from a base unit 129. In the example depicted, the arm unit 131 includes joint portions 133a, 133b and 133c and links 135a and 135b and is driven under the control of an arm controlling apparatus 145. The endoscope 101 is supported by the arm unit 131 such that the position and the posture of the endoscope 101 are controlled. Consequently, stable fixation in position of the endoscope 101 can be implemented.

(Endoscope)

The endoscope 101 includes the lens barrel 103 which has a region of a predetermined length from a distal end thereof to be inserted into a body cavity of the patient 171, and a camera head 105 connected to a proximal end of the lens barrel 103. In the example depicted, the endoscope 101 is depicted as a rigid endoscope having the lens barrel 103 of the hard type. However, the endoscope 101 may otherwise be configured as a flexible endoscope having the lens barrel 103 of the flexible type.

The lens barrel 103 has, at a distal end thereof, an opening in which an objective lens is fitted. A light source apparatus 143 is connected to the endoscope 101 such that light generated by the light source apparatus 143 is introduced to a distal end of the lens barrel by a light guide extending in the inside of the lens barrel 103 and is emitted toward an observation target (in other words, an image pickup target) in a body cavity of the patient 171 through the objective lens. It is to be noted that the endoscope 101 may be a forward-viewing endoscope or may be an oblique-viewing endoscope or a side-viewing endoscope.

An optical system and an image pickup element are provided in the inside of the camera head 105 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a camera control unit (CCU) 139. It is to be noted that the camera head 105 has a function incorporated therein for suitably driving the optical system of the camera head 105 to adjust the magnification and the focal distance.

It is to be noted that, in order to establish compatibility with, for example, a stereoscopic vision (three-dimensional (3D) display), a plurality of image pickup elements may be provided on the camera head 105. In this case, a plurality of relay optical systems is provided in the inside of the lens barrel 103 in order to guide observation light to each of the plurality of image pickup elements.

(Various Apparatus Incorporated in Cart)

The CCU 139 includes a central processing unit (CPU), a graphics processing unit (GPU) or the like and integrally controls operation of the endoscope 101 and the display apparatus 141. In particular, the CCU 139 performs, for an image signal received from the camera head 105, various image processes for displaying an image based on the image signal such as, for example, a development process (demosaic process). The CCU 139 provides the image signal for which the image processes have been performed to the display apparatus 141. Further, the CCU 139 transmits a control signal to the camera head 105 to control driving of the camera head 105. The control signal can include information relating to an imaging condition such as a magnification or a focal distance.

The display apparatus 141 displays an image based on an image signal for which the image processes have been performed by the CCU 139 under the control of the CCU 139. In a case where the endoscope 101 is ready for imaging of a high resolution such as 4K (horizontal pixel number 3840×vertical pixel number 2160), 8K (horizontal pixel number 7680×vertical pixel number 4320) or the like and/or ready for 3D display, then a display apparatus by which corresponding display of the high resolution and/or 3D display are possible can be used as the display apparatus 141. In a case where the apparatus is ready for imaging of a high resolution such as 4K or 8K, if the display apparatus used as the display apparatus 141 has a size of equal to or not less than 55 inches, then a more immersive experience can be obtained. Further, a plurality of display apparatuses 141 having different resolutions and different sizes may be provided in accordance with purposes.

The light source apparatus 143 includes a light source such as, for example, a light emitting diode (LED) and supplies irradiation light for imaging of a surgical region to the endoscope 101.

The arm controlling apparatus 145 includes a processor such as, for example, a CPU and operates in accordance with a predetermined program to control driving of the arm unit 131 of the supporting arm apparatus 127 in accordance with a predetermined controlling method.

An input apparatus 147 is an input interface for the endoscopic surgery system 100. A user can perform inputting of various kinds of information or instruction inputting to the endoscopic surgery system 100 through the input apparatus 147. For example, the user would input various kinds of information relating to surgery such as physical information of a patient, information regarding a surgical procedure of the surgery and so forth through the input apparatus 147. Further, the user would input, for example, an instruction to drive the arm unit 131, an instruction to change an imaging condition (type of irradiation light, magnification, focal distance or the like) by the endoscope 101, an instruction to drive the energy device 121 or the like through the input apparatus 147.

The type of the input apparatus 147 is not limited and may be that of any one of various known input apparatuses. As the input apparatus 147, for example, a mouse, a keyboard, a touch panel, a switch, a foot switch 157 and/or a lever or the like can be applied. In a case where a touch panel is used as the input apparatus 147, it may be provided on the display face of the display apparatus 141.

Otherwise, the input apparatus 147 is a device to be mounted on a user such as, for example, a glasses type wearable device or a head mounted display (HMD), and various kinds of inputting are performed in response to a gesture or a line of sight of the user detected by any of the devices mentioned. Further, the input apparatus 147 includes a camera which can detect a motion of a user, and various kinds of inputting are performed in response to a gesture or a line of sight of a user detected from a video picked up by the camera. Further, the input apparatus 147 includes a microphone which can collect the voice of a user, and various kinds of inputting are performed by voice collected by the microphone. By configuring the input apparatus 147 such that various kinds of information can be inputted in a contactless fashion in this manner, especially a user who belongs to a clean area (for example, the surgeon 167) can operate an apparatus belonging to an unclean area in a contactless fashion. Further, since the user can operate an apparatus without releasing a possessed surgical tool from its hand, the convenience to the user is improved.

A treatment tool controlling apparatus 149 controls driving of the energy device 121 for cautery or incision of a tissue, sealing of a blood vessel or the like. A pneumoperitoneum apparatus 151 feeds gas into a body cavity of the patient 171 through the pneumoperitoneum tube 119 to inflate the body cavity in order to secure the field of view of the endoscope 101 and secure the working space for the surgeon. A recorder 153 is an apparatus capable of recording various kinds of information relating to surgery. A printer 155 is an apparatus capable of printing various kinds of information relating to surgery in various forms such as a text, an image or a graph.

In the following, especially a characteristic configuration of the endoscopic surgery system 100 is described in more detail.

(Supporting Arm Apparatus)

The supporting arm apparatus 127 includes the base unit 129 serving as a base, and the arm unit 131 extending from the base unit 129. In the example depicted, the arm unit 131 includes the plurality of joint portions 133*a*, 133*b* and 133*c* and the plurality of links 135*a* and 135*b* connected to each other by the joint portion 133*b*. In FIG. 1, for simplified illustration, the configuration of the arm unit 131 is depicted in a simplified form. Actually, the shape, number and arrangement of the joint portions 133*a* to 133*c* and the links 135*a* and 135*b* and the direction and so forth of axes of rotation of the joint portions 133a to 133c can be set suitably such that the arm unit 131 has a desired degree of freedom. For example, the arm unit 131 can preferably be configured such that it has a degree of freedom equal to or not less than 6 degrees of freedom. This makes it possible to move the endoscope 101 freely within the movable range of the arm unit 131. Consequently, it becomes possible to insert the lens barrel 103 of the endoscope 101 from a desired direction into a body cavity of the patient 171.

An actuator is provided in each of the joint portions 133a to 133c, and the joint portions 133a to 133c are configured such that they are rotatable around predetermined axes of rotation thereof by driving of the respective actuators. The driving of the actuators is controlled by the arm controlling apparatus 145 to control the rotational angle of each of the joint portions 133a to 133c thereby to control driving of the arm unit 131. Consequently, control of the position and the posture of the endoscope 101 can be implemented. Thereupon, the arm controlling apparatus 145 can control driving of the arm unit 131 by various known controlling methods such as force control or position control.

For example, if the surgeon 167 suitably performs operation inputting through the input apparatus 147 (including the foot switch 157), then driving of the arm unit 131 may be controlled suitably by the arm controlling apparatus 145 in response to the operation input to control the position and the posture of the endoscope 101. After the endoscope 101 at the distal end of the arm unit 131 is moved from an arbitrary position to a different arbitrary position by the control just described, the endoscope 101 can be supported fixedly at the position after the movement. It is to be noted that the arm unit 131 may be operated in a master-slave fashion. In this case, the arm unit 131 can be remotely controlled by the user through the input apparatus 147 which is placed at a place remote from the operating room.

Further, in a case where force control is applied, the arm controlling apparatus 145 may perform power-assisted control to drive the actuators of the joint portions 133a to 133c such that the arm unit 131 may receive external force by the user and move smoothly following the external force. This makes it possible to move, when the user directly touches with and moves the arm unit 131, the arm unit 131 with comparatively weak force. Accordingly, it becomes possible for the user to move the endoscope 101 more intuitively by a simpler and easier operation, and the convenience to the user can be improved.

Here, generally in endoscopic surgery, the endoscope 101 is supported by a medical doctor called scopist. In contrast, where the supporting arm apparatus 127 is used, the position of the endoscope 101 can be fixed more certainly without hands, and therefore, an image of a surgical region can be obtained stably and surgery can be performed smoothly.

It is to be noted that the arm controlling apparatus 145 may not necessarily be provided on the cart 137. Further, the arm controlling apparatus 145 may not necessarily be a single apparatus. For example, the arm controlling apparatus 145 may be provided in each of the joint portions 133a to 133c of the arm unit 131 of the supporting arm apparatus 127 such that the plurality of arm controlling apparatus 145 cooperate with each other to implement driving control of the arm unit 131.

(Light Source Apparatus)

The light source apparatus 143 supplies irradiation light upon imaging of a surgical region to the endoscope 101. The light source apparatus 143 includes a white light source which includes, for example, an LED, a laser light source or a combination of them. In this case, in a case where a white light source includes a combination of RGB laser light sources, since the output intensity and the output timing can be controlled with a high degree of accuracy for each color (each wavelength), adjustment of the white balance of a picked up image can be performed by the light source apparatus 143. Further, in this case, if laser beams from the respective RGB laser light sources are emitted time-divisionally on an observation target and driving of the image pickup elements of the camera head 105 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 143 may be controlled such that the intensity of light to be outputted is changed for each predetermined time. By controlling driving of the image pickup element of the camera head 105 in synchronism with the timing of the change of the intensity of light to acquire images time-divisionally and synthesizing the images, an image of a high dynamic range free from so-called underexposed blocked up shadows and overexposed highlights can be created.

Further, the light source apparatus 143 may be configured to be capable of supplying light of a predetermined wavelength band ready for special light observation. In special light observation, for example, by utilizing the wavelength dependency of absorption of light in a body tissue to emit light of a narrower wavelength band in comparison with irradiation light upon ordinary observation (namely, white light), so-called narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by emission of excitation light may be performed. In fluorescent observation, it is possible to perform observation of fluorescent light from a body tissue by emitting excitation light on the body tissue (autofluorescence observation) or to obtain a fluorescent light image by locally injecting a reagent such as indocyanine green (ICG) into a body tissue and emitting excitation light corresponding to a fluorescent light wavelength of the reagent upon the body tissue. The light source apparatus 143 can be configured to be capable of supplying such narrow-band light and/or excitation light suitable for special light observation as described above.

(Camera Head and CCU)

Functions of the camera head 105 of the endoscope 101 and the CCU 139 are described in more detail with reference to FIG. 2. FIG. 2 is a block diagram depicting an example of a functional configuration of the camera head 105 and the CCU 139 depicted in FIG. 1.

Referring to FIG. 2, the camera head 105 has, as functions thereof, a lens unit 107, an image pickup unit 109, a driving unit 111, a communication unit 113 and a camera head controlling unit 115. Further, the CCU 139 has, as functions thereof, a communication unit 159, an image processing unit 161 and a control unit 163. The camera head 105 and the CCU 139 are connected to be bidirectionally communicable to each other by a transmission cable 165.

First, a functional configuration of the camera head 105 is described. The lens unit 107 is an optical system provided at a connecting location of the camera head 105 to the lens barrel 103. Observation light taken in from a distal end of the lens barrel 103 is introduced into the camera head 105 and enters the lens unit 107. The lens unit 107 includes a combination of a plurality of lenses including a zoom lens and a focusing lens. The lens unit 107 has optical properties adjusted such that the observation light is condensed on a light receiving face of the image pickup element of the image pickup unit 109. Further, the zoom lens and the focusing lens are configured such that the positions thereof on their optical axis are movable for adjustment of the magnification and the focal point of a picked up image.

The image pickup unit 109 includes an image pickup element and is disposed at a succeeding stage to the lens unit 107. Observation light having passed through the lens unit 107 is condensed on the light receiving face of the image pickup element, and an image signal corresponding to the observation image is generated by photoelectric conversion. The image signal generated by the image pickup unit 109 is provided to the communication unit 113.

As the image pickup element which is included by the image pickup unit 109, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 167 can comprehend a state of the surgical region in enhanced details and can proceed with the surgery more smoothly.

Further, the image pickup element which is included by the image pickup unit 109 is configured such that it has a pair of image pickup elements for acquiring image signals for the right eye and the left eye compatible with 3D display. Where 3D display is applied, the surgeon 167 can comprehend the depth of a living body tissue in the surgical region more accurately. It is to be noted that, if the image pickup unit 109 is configured as that of the multi-plate type, then a plurality of systems of lens units 107 is provided corresponding to the individual image pickup elements.

Further, the image pickup unit 109 may not necessarily be provided on the camera head 105. For example, the image pickup unit 109 may be provided just behind the objective lens in the inside of the lens barrel 103.

The driving unit 111 includes an actuator and moves the zoom lens and the focusing lens of the lens unit 107 by a predetermined distance along the optical axis under the control of the camera head controlling unit 115. Consequently, the magnification and the focal point of a picked up image by the image pickup unit 109 can be adjusted suitably.

The communication unit 113 includes a communication apparatus for transmitting and receiving various kinds of information to and from the CCU 139. The communication unit 113 transmits an image signal acquired from the image pickup unit 109 as RAW data to the CCU 139 through the transmission cable 165. Thereupon, in order to display a picked up image of a surgical region in low latency, preferably the image signal is transmitted by optical communication. This is because, upon surgery, the surgeon 167 performs surgery while observing the state of an affected area through a picked up image, it is demanded for a moving image of the surgical region to be displayed on the real time basis as far as possible in order to achieve surgery with a higher degree of safety and certainty. In a case where optical communication is applied, a photoelectric conversion module for converting an electric signal into an optical signal is provided in the communication unit 113. After the image signal is converted into an optical signal by the photoelectric conversion module, it is transmitted to the CCU 139 through the transmission cable 165.

Further, the communication unit 113 receives a control signal for controlling driving of the camera head 105 from the CCU 139. The control signal includes information relating to imaging conditions such as, for example, information that a frame rate of a picked up image is designated, information that an exposure value upon imaging is designated and/or information that a magnification and a focal point of a picked up image are designated. The communication unit 113 provides the received control signal to the camera head controlling unit 115. It is to be noted that also the control signal from the CCU 139 may be transmitted by optical communication. In this case, a photoelectric conversion module for converting an optical signal into an electric signal is provided in the communication unit 113. After the control signal is converted into an electric signal by the photoelectric conversion module, it is provided to the camera head controlling unit 115.

It is to be noted that the imaging conditions such as the frame rate, exposure value, magnification or focal point are set automatically by the control unit 163 of the CCU 139 on the basis of an acquired image signal. In other words, what is called an auto exposure (AE) function, an auto focus (AF) function and an auto white balance (AWB) function are incorporated in the endoscope 101.

The camera head controlling unit 115 controls driving of the camera head 105 on the basis of a control signal from the CCU 139 received through the communication unit 113. For example, the camera head controlling unit 115 controls driving of the image pickup element of the image pickup unit 109 on the basis of information that a frame rate of a picked up image is designated and/or information that an exposure value upon imaging is designated. Further, for example, the camera head controlling unit 115 suitably moves the zoom lens and the focus lens of the lens unit 107 through the driving unit 111 on the basis of information that a magnification and a focal point of a picked up image are designated. The camera head controlling unit 115 may further include a function for storing information for identifying the lens barrel 103 or the camera head 105.

It is to be noted that, by disposing the components such as the lens unit 107 and the image pickup unit 109 in a sealed structure having high airtightness and waterproof, the camera head 105 can be provided with resistance to an autoclave sterilization process.

Now, a functional configuration of the CCU 139 is described. The communication unit 159 includes a communication apparatus for transmitting and receiving various kinds of information to and from the camera head 105. The communication unit 159 receives an image signal transmitted thereto from the camera head 105 through the transmission cable 165. Thereupon, the image signal can be transmitted preferably by optical communication as described above. In this case, for the compatibility with optical communication, the communication unit 159 includes a photoelectric conversion module for converting an optical signal into an electric signal. The communication unit 159 provides the image signal after conversion into an electric signal to the image processing unit 161.

Further, the communication unit 159 transmits, to the camera head 105, a control signal for controlling driving of the camera head 105. The control signal may also be transmitted by optical communication.

The image processing unit 161 performs various image processes for an image signal in the form of RAW data transmitted thereto from the camera head 105. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 161 performs a detection process for an image signal in order to perform AE, AF and AWB.

The image processing unit 161 includes a processor such as a CPU or a GPU, and when the processor operates in accordance with a predetermined program, the image processes and the detection process described above can be performed. It is to be noted that, in a case where the image processing unit 161 includes a plurality of GPUs, the image processing unit 161 suitably divides information relating to an image signal such that image processes are performed in parallel by the plurality of GPUs.

The control unit 163 performs various kinds of control relating to imaging of a surgical region by the endoscope 101 and display of the picked up image. For example, the control unit 163 generates a control signal for controlling driving of the camera head 105. Thereupon, in a case where imaging conditions are inputted by the user, then the control unit 163 generates a control signal on the basis of the input by the user. Alternatively, in a case where the endoscope 101 has an AE function, an AF function and an AWB function incorporated therein, the control unit 163 suitably calculates an optimum exposure value, focal distance and white balance in response to a result of a detection process by the image processing unit 161 and generates a control signal.

Further, the control unit 163 controls the display apparatus 141 to display an image of a surgical region on the basis of an image signal for which image processes have been performed by the image processing unit 161. Thereupon, the control unit 163 recognizes various objects in the surgical region image using various image recognition technologies. For example, the control unit 163 can recognize a surgical tool such as forceps, a particular living body region, bleeding, mist when the energy device 121 is used and so forth by detecting the shape, color and so forth of edges of the objects included in the surgical region image. The control unit 163 causes, when it controls the display apparatus 141 to display a surgical region image, various kinds of surgery supporting information to be displayed in an overlapping manner with an image of the surgical region using a result of the recognition. Where surgery supporting information is displayed in an overlapping manner and presented to the surgeon 167, the surgeon 167 can proceed with the surgery more safety and certainty.

The transmission cable 165 which connects the camera head 105 and the CCU 139 to each other is an electric signal cable ready for communication of an electric signal, an optical fiber ready for optical communication or a composite cable ready for both of electrical and optical communication.

Here, while, in the example depicted, communication is performed by wired communication using the transmission cable 165, the communication between the camera head 105 and the CCU 139 may be performed otherwise by wireless communication. In a case where the communication between the camera head 105 and the CCU 139 is performed by wireless communication, there is no necessity to lay the transmission cable 165 in the operating room. Therefore, such a situation that movement of medical staff in the operating room is disturbed by the transmission cable 165 can be eliminated.

An example of the endoscopic surgery system 100 to which the technology according to an embodiment of the present disclosure can be applied has been described above. It is to be noted here that, although the endoscopic surgery system 100 has been described as an example, the system to which the technology according to an embodiment of the present disclosure can be applied is not limited to the example. For example, the technology according to an embodiment of the present disclosure may be applied to a flexible endoscopic system for inspection or a microscopic surgery system.

2. EXAMINATION OF AUTO FLUORESCENCE IMAGING

Next, a technical problem of the imaging system according to the present embodiment will be described after describing an example of a fluorescent material used for auto fluorescence imaging with regard to the auto fluorescence imaging in which a fluorescent image of a lesion portion is observed using the fluorescent material, among observation methods called special light observation.

In auto fluorescence imaging, a fluorescent material having an affinity for a lesion such as cancer is previously administered to an examination target person (patient), and excitation light for exciting the fluorescent material is emitted to observe a lesion portion using a fluorescent image of fluorescence emitted from the fluorescent material accumulated in the lesion portion (that is, an observation image based on a result of detection of fluorescence). A representative example of a fluorescent material used for auto fluorescence imaging is indocyanine green (ICG). ICG emits fluorescence having a wavelength of approximately 820 nm (that is, light in a near-infrared band) by using light having a wavelength of approximately 808 nm as excitation light.

Further, in recent years, as fluorescent materials used for auto fluorescence imaging, various fluorescent materials other than ICG have also been proposed from the viewpoint of characteristics of more selective accumulation on lesions such as cancer and a reduction in the influence (an adverse reaction) on an examination target person with administration. In addition, among such fluorescent materials, a fluorescent material emitting fluorescence in a wavelength band different from that of ICG has also been proposed, and a fluorescent material emitting light belonging to a visible light wavelength band has also been proposed. For example, FIG. 3 is a view depicting an example of a relationship between various fluorescent materials used for auto fluorescence imaging and wavelength bands of fluorescence emitted by the fluorescent materials.

Figure 3:
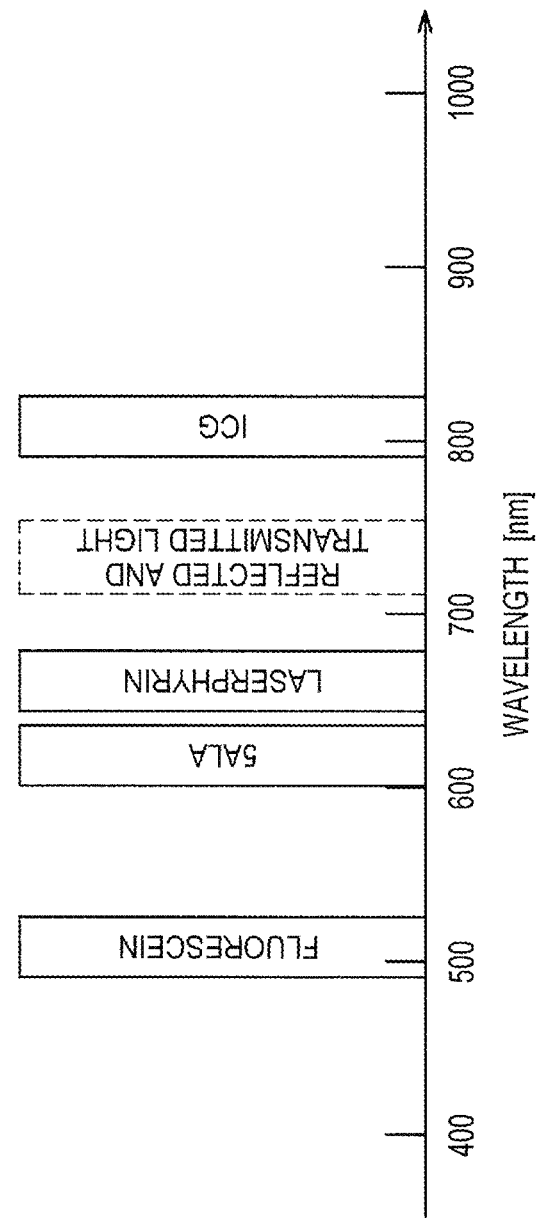
FIG. 3 is a view depicting an example of a relationship between various fluorescent materials used for auto fluorescence imaging and wavelength bands of fluorescence emitted by the fluorescent materials.

As a specific example, as depicted in FIG. 3, in addition to ICG fluorescent materials emitting fluorescence in a band of visible light such as fluorescein, 5-aminolevulinic acid (5ALA), and laserphyrin have also been proposed as fluorescent materials used for auto fluorescence imaging. More specifically, fluorescein emits fluorescence in a visible light region (particularly, a wavelength band of a G component) of approximately 520 nm. In addition, 5ALA emits fluorescence in a visible light region (particularly, a wavelength band of an R component) of approximately 635 nm. In addition, laserphyrin emits fluorescence in the vicinity of a wavelength band of 670 nm to 730 nm, that is, fluorescence from a visible light region (particularly, in the vicinity of a near-infrared region) to a near-infrared region. In addition, the examples of the fluorescent materials depicted in FIG. 3 are only examples, and various fluorescent materials other than the examples depicted in FIG. 3 have also been proposed. In particular, a near-infrared wavelength band in the vicinity of 650 nm to 1000 nm is known as a wavelength band in which light easily passes through a living body, and is also called a "biological window". For example, regarding a wavelength band depicted as "reflected and transmitted light", FIG. 3 schematically depicts a wavelength band of light used in an analysis method for analyzing components of a material serving as an observation target (in other words, an image pickup target) by emitting light in a predetermined wavelength band (particularly, light belonging to the biological window) as in so-called near-infrared spectroscopy or the like. For example, as fluorescent materials allowing a deeper portion in the body of an examination target person to be observed using such characteristics, various fluorescent materials emitting fluorescence belonging to the biological window and a fluorescent material emitting fluorescence belonging to a wavelength band in the vicinity of the biological window have also been proposed.

On the other hand, in auto fluorescence imaging, there is a tendency to use an image pickup apparatus (for example, a camera head) corresponding to a fluorescent material to be used for the pickup of a fluorescent image of fluorescence emitted from the fluorescent material. Specifically, the fluorescence emitted from the fluorescent material tends to have lower light intensity than other light such as visible light condensed together with the fluorescence and excitation light of the fluorescent material. For this reason, the image pickup apparatus may be provided with, for example, a unique component (for example, a branching optical system, a filter, or the like) for separating at least a portion of a wavelength band in a wavelength band of fluorescence emitted from a fluorescent material and light (for example, visible light or excitation light) in another wavelength band different from light in the wavelength band. That is, a dedicated image pickup apparatus is often used for auto fluorescence imaging using a predetermined fluorescent material in order to observe a fluorescent image of fluorescence emitted from the fluorescent material.

However, in a use mode in which a dedicated image pickup apparatus (camera head) is used for each fluorescent material in a situation where various fluorescent materials (that is, a plurality of types of fluorescent materials) are selectively used without being limited to ICG, the image pickup apparatus is required to be attached and detached, which can make an operation related to auto fluorescence imaging more complicated. Further, it is necessary to prepare an image pickup apparatus for each fluorescent material to be used, which can result in an increase in costs. For this reason, the present disclosure proposes an imaging system which is capable of picking up a fluorescent image, corresponding to a fluorescent material to be used, even in a situation where a plurality of types of fluorescent materials is selectively used by making it possible to observe fluorescence emitted from each of a plurality of types of fluorescent materials with one image pickup apparatus.

3. TECHNICAL FEATURES

Next, technical features of the imaging system according to the embodiment of the present disclosure will be described below.

3.1. Schematic Configurations of Camera Head and Light Source Apparatus

Figure 4:
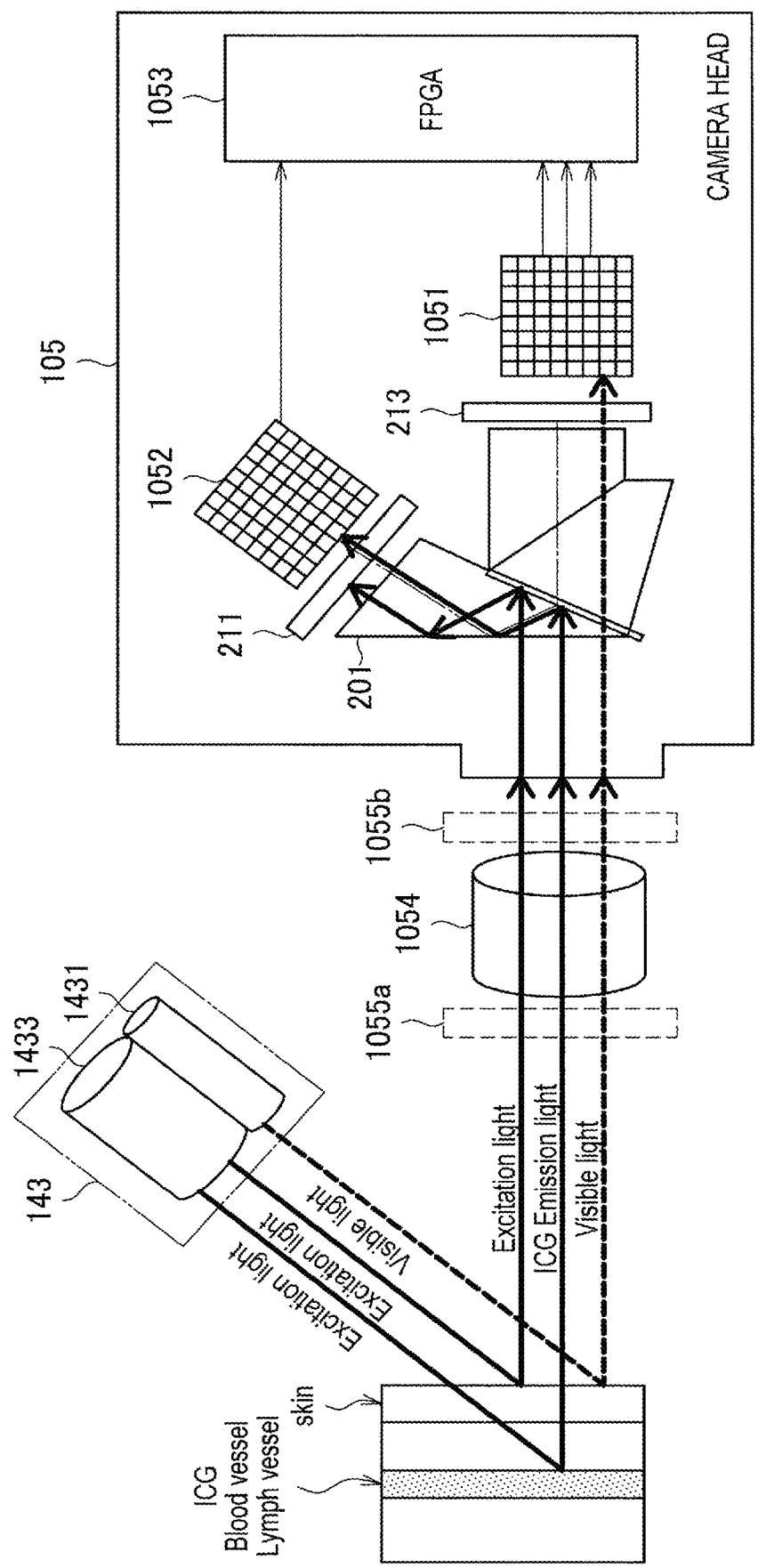
FIG. 4 is a view depicting an example of schematic configurations of a camera head and a light source apparatus in an imaging system according to the embodiment.

First, an example of schematic configurations of a camera head and a light source apparatus in the imaging system according to the present embodiment will be described. For example, FIG. 4 is a view depicting an example of schematic configurations of a camera head and a light source apparatus in an imaging system according to the embodiment. Note that, in the example depicted in FIG. 4, in order to facilitate the understanding of the configurations of the camera head and the light source apparatus, the description will focus on a case in which a fluorescent material administered to an examination target person in advance is irradiated with excitation light from the skin without using an endoscope or the like to pick up a fluorescent image of fluorescence emitted from the fluorescent material, as an example of a simpler configuration. Further, in the example depicted in FIG. 4, the description focuses on the light source apparatus 143 and the camera head 105 in the imaging system according to the present embodiment, and other components are not depicted in the drawing. Note that, in the endoscopic image pickup system, strictly different portions can also be present as in a case in which some components such as an endoscope (lens barrel) are inserted into the body cavity of an examination target person, but the schematic configuration thereof is the same as that in the example depicted in FIG. 4.

(Light Source Apparatus)

First, an example of a configuration of the light source apparatus 143 will be described. As depicted in FIG. 4, the light source apparatus 143 according to the present embodiment includes a visible light source 1431 that emits light (equivalent to an example of "first light") belonging to a visible light wavelength band and a near-infrared light source 1433 that emits light (equivalent to an example of "second light") belonging to a near-infrared wavelength band.

The visible light source 1431 is configured to be capable of emitting light continuously distributed in a visible light wavelength band. In addition, the visible light source 1431 is configured to be capable of emitting light having a peak of which the intensity is equal to or greater than a predetermined threshold value at at least one or more predetermined wavelength positions in a visible light wavelength band, and is configured to be capable of controlling the output (that is, intensity) of light corresponding to at least some wavelength positions among the at least one or more wavelength positions.

Figure 5:
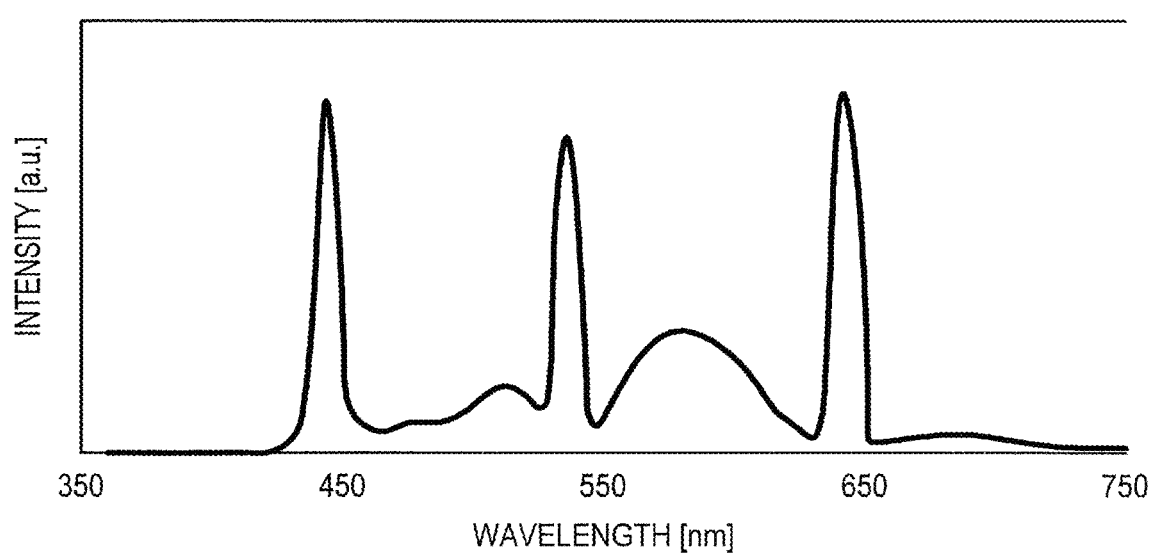
FIG. 5 is a view depicting an example of a spectrum of light belonging to a visible light wavelength band and emitted from the light source apparatus according to the embodiment.

For example, FIG. 5 depicts an example of a spectrum of light belonging to a visible light wavelength band and emitted from the light source apparatus according to the embodiment, and is equivalent to a spectrum of light emitted by the visible light source 1431. In FIG. 5, the horizontal axis represents a wavelength, and the vertical axis represents the intensity of light by a relative value. In the example depicted in FIG. 5, the visible light source 1431 is configured to be capable of emitting light (equivalent to an example of "fourth light") which is continuously distributed in a visible light wavelength band and light (equivalent to an example of "third light") which has a peak of which the intensity is higher than that of the light continuously distributed at a wavelength position in a wavelength band corresponding to each of an R component, a G component, and a B component.

More specifically, the visible light source 1431 includes a laser light source (equivalent to "an RGB laser light source") which is configured to be capable of outputting light having a peak at a wavelength position in a wavelength band of each of the R component, the G component, and the B component, and an LED light source (equivalent to "a white light source", and hereinafter, also referred to as "a white LED")

which is configured to be capable of outputting white light. Note that, in the following description, light having a peak at a wavelength position in a wavelength band corresponding to each of an R component, a G component, and a B component emitted by the RGB laser light source may be simply referred to as "an R component", "a G component", and "a B component".

Note that the visible light source 1431 may be configured to be capable of independently controlling the output of the RGB laser light source and the output of the white light source (white LED). In addition, the RGB laser light source may be configured to be capable of controlling the output of at least some components among the R component, the G component, and the B component such as temporary attenuation or temporary turn-off of the output. More specifically, the RGB laser light source is configured to be capable of controlling the output of light corresponding to at least a wavelength position which is included in a wavelength band of fluorescence emitted from a predetermined fluorescent material (particularly, a fluorescent material emitting fluorescence belonging to a visible light wavelength band) among the R component, the G component, and the B component or which is positioned in the vicinity of the wavelength band of the fluorescence.

As a specific example, the RGB laser light source may be configured to be capable of controlling the output of an R component as light at a wavelength position which is included in a wavelength band of fluorescence emitted from a fluorescent material, such as 5ALA or laserphyrin, or which is positioned in the vicinity of the wavelength band of the fluorescence. In addition, as another example, the RGB laser light source may be configured to be capable of controlling the output of a G component as light at a wavelength position which is included in a wavelength band of fluorescence emitted from a fluorescent material, such as fluorescein, or which is positioned in the vicinity of the wavelength band of the fluorescence. Naturally, the RGB laser light source may be configured to be capable of individually controlling the output of each of the R component, the G component, and the B component or to be capable of performing control to be associated with at least two or more components. In addition, the RGB laser light source may be configured to be capable of performing control so that the output of each of the R component, the G component, and the B component changes continuously, or may be configured to be capable of switching between the turn-on and turn-off of the output.

The near-infrared light source 1433 includes a light source which emits light in a near-infrared wavelength band (that is, "a near-infrared light source"), and is configured to be capable of emitting light in at least a portion of a wavelength band in the near-infrared wavelength band. More specifically, the near-infrared light source 1433 is configured to be capable of outputting light in a predetermined wavelength band including at least a portion of a wavelength band of an excitation wavelength of a predetermined fluorescent material (particularly, a fluorescent material excited by light belonging to a near-infrared wavelength band).

Based on such a configuration, in the imaging system according to the present embodiment, light belonging to a visible light wavelength band and light belonging to a near-infrared wavelength band are emitted toward an image pickup target from the light source apparatus 143. In this case, in the example depicted in FIG. 4, for example, light belonging to a visible light wavelength band is reflected from the surface of the skin of an examination target person and enters the camera head 105 through an optical system unit 1054 to be described later. Similarly, among light beams belonging to a near-infrared wavelength band, light not belonging to a biological window is reflected from the surface of the skin of the examination target person and enters the camera head 105 through the optical system unit 1054.

On the other hand, among light beams belonging to a near-infrared wavelength band, light belonging to a biological window reaches the inside of the body through the skin of the examination target person, and is emitted to tissues inside the body such as blood vessels or lymph vessels. In this case, a fluorescent material, such as ICG, which has been administered to the examination target person in advance and accumulated in some tissues (for example, a lesion or the like) is excited due to components in at least a portion of a wavelength band among light beams having reached the inside of the body of the examination target person, and fluorescence is emitted from the fluorescent material. The fluorescence which is emitted from the fluorescent material (that is, fluorescence belonging to a near-infrared wavelength band) is emitted to the outside of the body through the skin of the examination target person and enters the camera head 105 through the optical system unit 1054.

(Camera Head and Optical System Unit)

Next, an example of schematic configurations of the camera head 105 and the optical system unit 1054 will be described. As depicted in FIG. 4, the camera head 105 includes a branching optical system 201, filters 211 and 213, an image pickup element for picking up a visible light image 1051, an image pickup element for picking up a near-infrared light image 1052, and an FPGA 1053. The camera head 105 is configured such that the predetermined optical system unit 1054 can be mounted at the front stage of an incidence port toward the inside of the camera head 105. In addition, the camera head 105 is configured such that a notch filter 1055 can be mounted at the front stage of the incidence port toward the inside of the camera head 105. Note that the notch filter 1055 may be mounted at the front stage of the optical system unit 1054 as denoted by reference numeral 1055a. In addition, as another example, the notch filter 1055 may be mounted to be interposed between the optical system unit 1054 and the camera head 105 as denoted by reference numeral 1055b.

The optical system unit 1054 is a component for condensing external light and guiding the condensed light into the camera head 105. The optical system unit 1054 includes an imaging optical system constituted by, for example, a lens or the like, and causes the image pickup element for picking up the visible light image 1051 and the image pickup element for picking up the near-infrared light image 1052 which are provided inside the camera head 105 to image condensed light by the imaging optical system. In other words, the optical system unit 1054 generates an image of an image pickup target by taking in external light, and outputs the generated image to the camera head 105 positioned at the succeeding stage. In addition, the optical system unit 1054 may include an enlargement optical system that enlarges, for example, the generated image of the image pickup target. Specific examples of the optical system unit 1054 include a detachable lens unit, a lens barrel in an endoscope, an objective lens in a microscope, and the like.

The notch filter 1055 is configured to be detachable from the front stage of the camera head 105, and has a characteristic of blocking light in a portion of a wavelength band among light beams entering the camera head 105 through the optical system unit 1054. Note that a plurality of types of notch filters 1055 having different wavelength bands to be blocked may be selectively mounted on the camera head 105 or the optical system unit 1054. As a specific example, the notch filter 1055 blocking light in at least a portion of a wavelength band in an excitation wavelength of a fluorescent material in accordance with the fluorescent material to be used may be mounted on the camera head 105 or the optical system unit 1054. With such a configuration, it is possible to block the incidence of excitation light of the fluorescent material on the inside of the camera head 105 by the notch filter 1055 while simultaneously picking up a fluorescent image of fluorescence emitted from the fluorescent material.

Light guided to the inside of the camera head 105 through the optical system unit 1054 is incident on the branching optical system 201. The branching optical system 201 is constituted by, for example, a prism including a dichroic film therein, and separates (branches) incident light into light belonging to a visible light wavelength band and light belonging to a near-infrared wavelength band. In addition, the branching optical system 201 guides the separated light belonging to the visible light wavelength band to the image pickup element for picking up the visible light image 1051, and guides the separated light belonging to the near-infrared wavelength band to the image pickup element for picking up the near-infrared light image 1052.

In addition, the filter 211 is provided in a light path of the light (that is, a visible ray) which is separated by the branching optical system 201 and is guided to the image pickup element for picking up the visible light image 1051. The filter 211 mainly transmits light belonging to a visible light wavelength band, and has a characteristic of blocking at least light belonging to a near-infrared wavelength band.

In addition, a filter 213 is provided in a light path of the light (that is, a near-infrared ray) which is separated by the branching optical system 201 and is guided to the image pickup element for picking up the near-infrared light image 1052. The filter 213 mainly transmits light belonging to a wavelength band including at least a portion of a wavelength band of fluorescence emitted from a predetermined fluorescent material (specifically, a fluorescent material emitting fluorescence in a near-infrared wavelength band such as ICG) in a near-infrared wavelength band, and has a characteristic of blocking at least light belonging to a visible light wavelength band.

Note that more details of a configuration corresponding to each of the notch filter 1055, the branching optical system 201, and the filters 211 and 213 will be separately described later with specific examples.

The image pickup element for picking up the visible light image 1051 is an image pickup element which is provided at the stage after the branching optical system 201 and the filter 211 and on which light separated by the branching optical system 201 and belonging to a visible light wavelength band and having passed through the filter 211 is imaged. As the image pickup element for picking up the visible light image 1051, an image pickup element such as a CCD or a CMOS including an RGB color filter can be applied.

The image pickup element for picking up the near-infrared light image 1052 is an image pickup element which is provided at the stage after the branching optical system 201 and the filter 213 and on which light separated by the branching optical system 201 and belonging to at least a portion of a wavelength band (in other words, a wavelength band including at least a portion of a wavelength band of fluorescence emitted from a predetermined fluorescent material) in a near-infrared wavelength band and having passed through the filter 213 is imaged. It is preferable that an image pickup element having higher sensitivity be applied as the image pickup element for picking up the near-infrared light image 1052, and an image pickup element such as a CCD or a CMOS not provided with a color filter may be applied.

The field-programmable gate array (FPGA) 1053 is equivalent to a control unit that controls various operations of the camera head 105, and generates an image of an image pickup target on the basis of an image pickup result of each of the image pickup element for picking up the visible light image 1051 and the image pickup element for picking up the near-infrared light image 1052. As a specific example, the FPGA 1053 generates a visible light image of an image pickup target on the basis of an image pickup result obtained by the image pickup element for picking up the visible light image 1051. In addition, the FPGA 1053 generates a near-infrared light image of an image pickup target on the basis of an image pickup result obtained by the image pickup element for picking up the near-infrared light image 1052. Note that, in a case in which a fluorescent material emitting fluorescence belonging to a near-infrared wavelength region such as ICG is used, for example, it is possible to obtain a fluorescence image of fluorescence emitted by the fluorescent material as the near-infrared light image generated by the image pickup element for picking up the near-infrared light image 1052. In addition, the FPGA 1053 may generate an image in which a near-infrared light image (in other words, a fluorescence image) based on the image pickup result obtained by the image pickup element for picking up the near-infrared light image 1052 is superimposed on a visible light image based on the image pickup result obtained by the image pickup element for picking up the visible light image 1051.

Note that it is more preferable that the image pickup element for picking up the visible light image 1051 be disposed such that an optical axis of a visible ray emitted from the branching optical system 201 and having passed through the filter 211 is imaged in the center thereof. In addition, regarding the image pickup element for picking up the near-infrared light image 1052, it is more preferable that a fixed position be determined while performing shift adjustment in a direction perpendicular to an optical axis so that a screen deviation of a near-infrared light image with respect to a visible light image generated on the basis of the image pickup result of the image pickup element for picking up the visible light image 1051 is minimized. With such a configuration, it is possible to perform alignment of the visible light image and the near-infrared light image (fluorescence image) more simply at the time of superimposing the images on each other. In addition, as another example, the magnitude of a screen deviation of a near-infrared light image (fluorescence image) with respect to a visible light image generated due to a product error may be specified in advance after determining a fixed position of the image pickup element for picking up the near-infrared light image 1052 without performing the above-described position adjustment, and a read-out starting position of a near-infrared light image signal may be shifted so that the specified magnitude of the screen deviation is minimized. It is possible to omit the above-described adjustment processing by adopting a method of adjusting a read-out starting position, which leads to an advantage in terms of costs.

An example of schematic configurations of the camera head and the light source apparatus in the imaging system according to the present embodiment has been described above with reference to FIGS. 4 and 5. Note that an example of a more detailed configuration of a camera head in the imaging system according to the present embodiment will be described below with regard to a case in which the camera head is configured as a two-plate type camera head and a case in which the camera head is configured as a three-plate type camera head.

3.2. Configuration Example 1 of Two-Plate Type Camera Head

Figure 6:
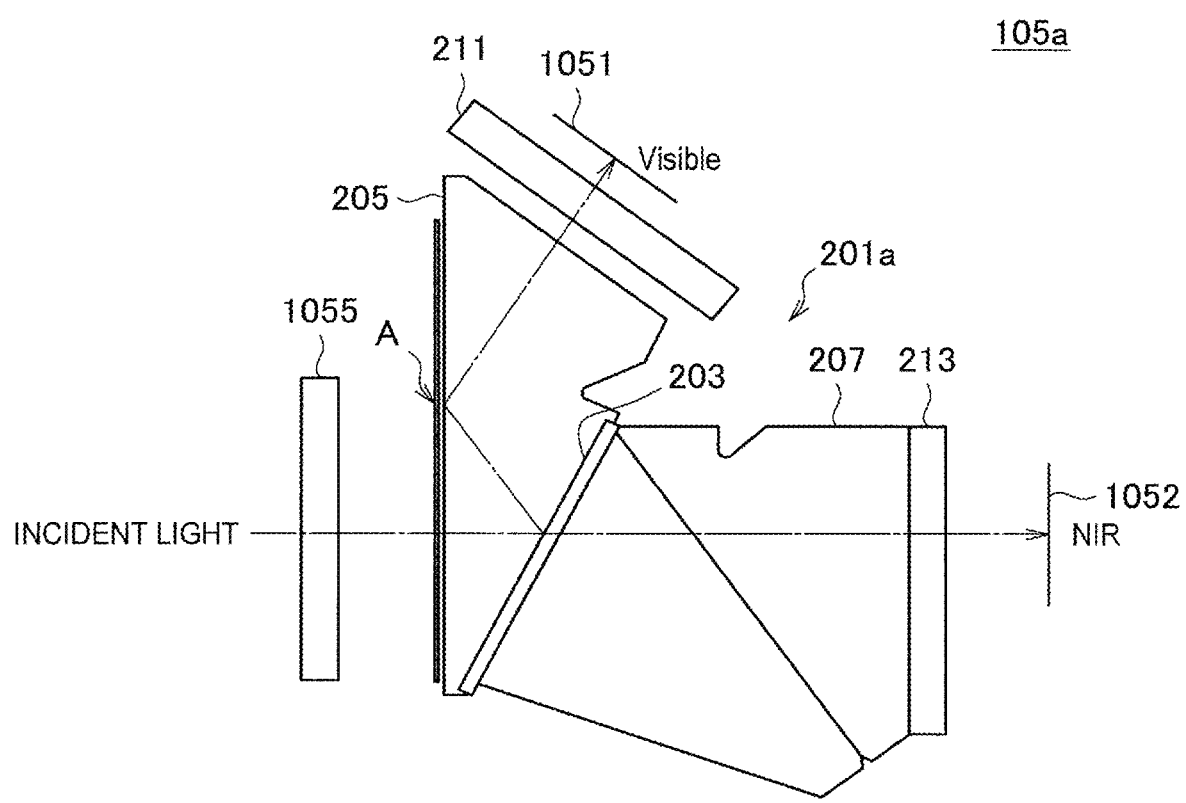
FIG. 6 is a schematic view depicting an example of a configuration of the camera head according to the embodiment.

First, as an example of a configuration of a camera head in the imaging system according to the present embodiment, a description will be given of an example of a configuration of a two-plate type camera head, particularly, focusing on a configuration until incident light is imaged on an image pickup element through a branching optical system. For example, FIG. 6 is a schematic view depicting an example of a configuration of a camera head according to the present embodiment. Note that, in the following description, the camera head 105 depicted in FIG. 6 may be referred to as "a camera head 105*a*" in a case in which the camera head 105 is expressly shown.

As depicted in FIG. 6, the camera head 105*a* includes a color separation prism 201*a*, an image pickup element for picking up the visible light image 1051, an image pickup element for picking up the near-infrared light image 1052, a notch filter 1055, a short pass filter 211, and a long pass filter 213. Note that the image pickup element for picking up the visible light image 1051 and the image pickup element for picking up the near-infrared light image 1052 have the same configurations as those of the image pickup element for picking up the visible light image 1051 and the image pickup element for picking up the near-infrared light image 1052 described with reference to FIG. 4, and thus a detailed description thereof will be omitted.

The color separation prism 201*a* is an optical member that separates incident light incident on the camera head 105*a* into light belonging to a visible light wavelength band and light belonging to a near-infrared wavelength band, and is equivalent to an example of the branching optical system 201 depicted in FIG. 4. In addition, a dichroic film 203 for separating light belonging to a visible light wavelength band and light belonging to a near-infrared wavelength band from each other is provided inside the color separation prism 201*a*.

Specifically, as depicted in FIG. 6, the color separation prism 201*a* is a prism in which a first prism 205 and a second prism 207 are bonded to each other through the dichroic film 203. That is, the dichroic film 203 is provided at an interface between the first prism 205 and the second prism 207.

The dichroic film 203 is an optical film that separates incident light incident on the color separation prism 201*a* and including light belonging to a visible light wavelength band and light belonging to a near-infrared wavelength band into light belonging to a visible light wavelength band and light belonging to a near-infrared wavelength band. Specifically, the dichroic film 203 has a characteristic of reflecting light belonging to a visible light wavelength band and transmitting light belonging to a near-infrared wavelength band. Note that details of spectral characteristics of the dichroic film 203 will be separately described later.

The first prism 205 is a prism functioning as a light path for visible light on which light belonging to a visible light wavelength band and light belonging to a near-infrared wavelength band is incident (that is, incident light) are incident and through which light belonging to a visible light wavelength band is guided. In addition, the second prism 207 is a prism functioning as a light path for near-infrared light to which light belonging to a near-infrared wavelength band is guided.

Incident light incident on the first prism 205 travels straight inside the first prism 205 and is separated into light belonging to a visible light wavelength band and light belonging to a near-infrared wavelength band by the dichroic film 203 which is obliquely provided on the optical axis thereof.

The light belonging to a visible light wavelength band is reflected by the dichroic film 203 and is guided to the inside of the first prism 205. Here, the reflected and separated light belonging to a visible light wavelength band (that is, a visible ray) is totally reflected at a position A depicted in FIG. 6 only once and is transmitted to the outside of the first prism 205. Thereby, it is possible to bring an angle of a film formation surface of the dichroic film 203 with respect to the optical axis close to a right angle. Conversely, an installation angle on the optical axis of the dichroic film 203 according to the present embodiment is set such that a total reflection condition of visible rays at the position A is established. The dichroic film 203 is disposed in this manner, so that it is possible to suppress changes in spectral characteristics of the dichroic film 203 due to a difference in an incidence angle between an upper light beam and a lower light beam and to perform wavelength separation with a high level of accuracy even when a bright light beam having an F value is incident on the first prism 205.

Visible rays having passed through the first prism 205 are guided to the image pickup element for picking up the visible light image 1051. In this case, the short pass filter 211 is provided in a light path of light which is separated by the dichroic film 203 and is imaged on the image pickup element for picking up the visible light image 1051. The short pass filter 211 transmits light (that is, light including visible light) having a wavelength equal to or less than a boundary between a visible light wavelength band and a near-infrared wavelength band with 750 nm as the boundary therebetween, and blocks light (that is, light including near-infrared light) having a wavelength exceeding the boundary. With such a configuration, it is possible to exclude infrared light included in visible rays having passed through the first prism 205 and to improve color reproducibility of a visible light image.

On the other hand, light belonging to a near-infrared wavelength band and having passed through the dichroic film 203 is incident on the second prism 207 and travels straight inside the second prism 207. An end surface (in other words, an emitting surface on a downstream side of the optical axis of the second prism 207) on a side opposite to the side where the dichroic film 203 is provided in the second prism 207 is provided so as to be perpendicular to the optical axis, and light belonging to a near-infrared wavelength band is transmitted to the outside of the second prism 207 while maintaining a state where the light is perpendicular to the emitting surface of the second prism 207.

Near infrared rays having passed through the second prism 207 are guided to the image pickup element for picking up the near-infrared light image 1052. In this case, the long pass filter 213 is provided in a light path of light which is separated by the dichroic film 203 and is imaged on the image pickup element for picking up the near-infrared light image 1052. The long pass filter 213 has a characteristic of opposite polarity to that of the short pass filter 211. That is, the long pass filter 213 transmits light (that is, light including near-infrared light) having a wavelength equal to or greater than a boundary between a visible light wavelength band and a near-infrared wavelength band with 750 nm as the boundary therebetween, and blocks light (that is, light including visible light) having a wavelength less than the boundary. With such a configuration, it is possible to exclude visible light included in near infrared rays having passed through the second prism 207.

Note that a material of the color separation prism 201*a* according to the present embodiment is not particularly limited, and it is possible to appropriately use known optical glass or optical crystal in accordance with a wavelength of light guided to the inside of the color separation prism 201*a*.

In addition, the notch filter 1055 is configured to be detachable from the front stage of the color separation prism 201*a*. With such a configuration, for example, as the notch filter 1055, it is possible to mount a filter having a characteristic of blocking light in at least a portion of a wavelength band of an excitation wavelength of a fluorescent material in accordance with the fluorescent material to be used. As a more specific example, in a case in which ICG is used as a fluorescent material, a filter blocking light in the vicinity of 808 nm which is an excitation wavelength of ICG may be mounted as the notch filter 1055.

As an example of a configuration of a camera head in the imaging system according to the present embodiment, reference has been made to FIG. 6 above to describe an example of a configuration of a two-plate type camera head, particularly, focusing on a configuration until incident light is imaged on an image pickup element through a branching optical system. Note that the configuration of the camera head described in FIG. 6 is merely an example and is not necessarily limited to the example depicted in FIG. 6. For example, the installation position of the image pickup element for picking up the visible light image 1051 and the installation position of the image pickup element for picking up the near-infrared light image 1052 may be reversed. In this case, for example, as the dichroic film 203, a dichroic film having a characteristic of transmitting light belonging to a visible light wavelength band and reflecting light belonging to a near-infrared wavelength band may be applied. That is, the characteristic of the dichroic film 203 may be appropriately changed in accordance with a relationship between the installation position of the image pickup element for picking up the visible light image 1051 and the installation position of the image pickup element for picking up the near-infrared light image 1052.

Figure 7:
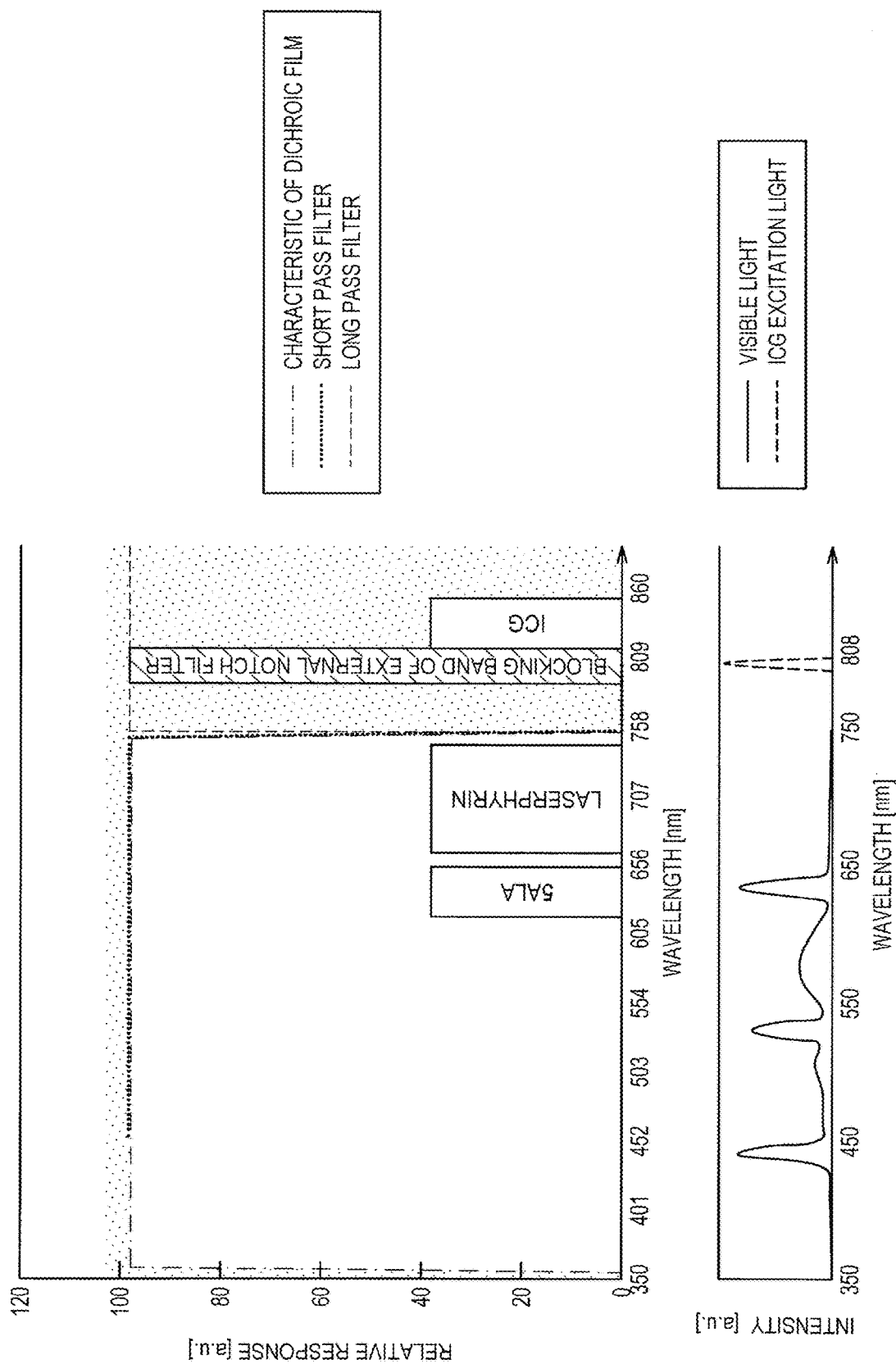
FIG. 7 is a view depicting an example of a relationship between spectral characteristics of a dichroic film and various filters according to the embodiment and a spectrum of light emitted from the light source apparatus.

Subsequently, spectral characteristics of the dichroic film 203, the notch filter 1055, the short pass filter 211, and the long pass filter 213 in the camera head 105*a* will be described with reference to FIG. 7. FIG. 7 is a view depicting an example of a relationship between spectral characteristics of a dichroic film and various filters according to the present embodiment and a spectrum of light emitted from a light source apparatus. For example, in the upper drawing of FIG. 7, spectral characteristics of the dichroic film 203, the notch filter 1055, the short pass filter 211, and the long pass filter 213 are schematically depicted. In the upper drawing of FIG. 7, the horizontal axis represents a wavelength, and the vertical axis represents characteristics according to transmission or reflection of the dichroic film and various filters by relative values (%). In addition, the lower drawing of FIG. 7 depicts a spectrum of light emitted from the light source apparatus according to the present embodiment. In the lower drawing of FIG. 7, the horizontal axis represents a wavelength, and the vertical axis represents characteristics according to transmission or reflection of the dichroic film and various filters by relative values (%). Note that, in FIG. 7, the position of the horizontal axis in the upper drawing and the position of the horizontal axis in the lower drawing correspond to each other. Further, in the present description, it is assumed that the light source apparatus emits light (that is, excitation light of ICG) in the vicinity of 808 nm which is an excitation wavelength of ICG as light in a near-infrared wavelength band. That is, in the example depicted in FIG. 7, a notch filter blocking light in the vicinity of 808 nm which is an excitation wavelength of ICG is applied as the notch filter 1055.

In FIG. 7, a graph plotted as dichroic film characteristics schematically depicts a wavelength band of each of light reflected by the dichroic film 203 depicted in FIG. 6 and light passing through the dichroic film 203. Specifically, the inner side of the graph plotted as dichroic film characteristics is equivalent to a component reflected by the dichroic film 203, and the outer side of the graph is equivalent to a component passing through the dichroic film 203. That is, the dichroic film 203 has a characteristic of reflecting most (for example, equal to or greater than 90%) of light in a wavelength band of 350 nm to 750 nm and transmitting most (for example, equal to or greater than 90%) of light in a wavelength band exceeding 750 nm.

In addition, a graph plotted as characteristics of the short pass filter schematically depicts a wavelength band of each of light passing through the short pass filter 211 depicted in FIG. 6 and light blocked by the short pass filter 211. As described above, the short pass filter 211 transmits light (that is, light including visible light) having a wavelength equal to or less than a boundary between a visible light wavelength band and a near-infrared wavelength band with 750 nm as a boundary therebetween, and blocks light (that is, light including near-infrared light) having a wavelength exceeding the boundary. With such a configuration, it is possible to image, for example, light, belonging to a visible light wavelength band, which is emitted from the visible light source 1431 of the light source apparatus 143 and is guided to the inside of the camera head 105*a* on the image pickup element for picking up the visible light image 1051 through the color separation prism 201*a* and the short pass filter 211.

In addition, a graph plotted as characteristics of the long pass filter schematically depicts a wavelength band of each of light passing through the long pass filter 213 depicted in FIG. 6 and light blocked by the long pass filter 213. As described above, the long pass filter 213 transmits light (that is, light including near-infrared light) having a wavelength equal to or greater than a boundary between a visible light wavelength band and a near-infrared wavelength band with 750 nm as the boundary therebetween, and blocks light (that is, light including visible light) having a wavelength less than the boundary. With such a configuration, it is possible to image, for example, light, belonging to a near-infrared light wavelength band, which is emitted from the near-infrared light source 1433 of the light source apparatus 143 and incident into the camera head 105*a* on the image pickup element for picking up the near-infrared light image 1052 through the color separation prism 201*a* and the long pass filter 213.

On the other hand, in the example depicted in FIG. 7, a filter blocking light in the vicinity of 808 nm which is an excitation wavelength of ICG is mounted at the front stage of the color separation prism 201*a* as the notch filter 1055. For this reason, light in the vicinity of 808 nm which is an excitation wavelength of ICG among light beams belonging to a near-infrared wavelength band which are guided to the inside of the camera head 105a, is blocked by the notch filter 1055.

Based on the above-described configuration, the camera head 105a can pick up, for example, a fluorescent image of fluorescence belonging to a near-infrared wavelength band and emitted from a fluorescent material such as ICG or a fluorescent image of fluorescence belonging to a visible light wavelength band and emitted from a fluorescent material such as 5ALA and laserphyrin.

As a specific example, a description will be given focusing on a case in which ICG is used as a fluorescent material. As depicted in FIG. 7, fluorescence emitted from ICG belongs to a near-infrared wavelength band, and thus the fluorescence is incident into the camera head 105a and is then imaged on the image pickup element for picking up the near-infrared light image 1052 through the color separation prism 201a and the long pass filter 213. In addition, excitation light of ICG is blocked by the notch filter 1055 before being incident into the camera head 105a. With such a configuration, it is possible to observe a fluorescent image of fluorescence emitted from ICG using a near-infrared light image generated on the basis of an image pickup result obtained by the image pickup element for picking up the near-infrared light image 1052. Further, in a case in which ICG is used as a fluorescent material, it is possible to pick up a visible light image of an image pickup target independently of a fluorescent image of fluorescence emitted from ICG on the basis of an image pickup result obtained by the image pickup element for picking up the visible light image 1051. For this reason, in this case, for example, it is also possible to superimpose the fluorescent image of fluorescence emitted from ICG on the visible light image of the image pickup target.

Subsequently, a description will be given focusing on a case in which 5ALA is used as a fluorescent material. As depicted in FIG. 7, fluorescence emitted from 5ALA belongs to a visible light wavelength band, and thus the fluorescence is incident into the camera head 105a and is then imaged on the image pickup element for picking up the visible light image 1051 through the color separation prism 201a and the short pass filter 211. On the other hand, at least a portion of a wavelength band of fluorescence emitted from 5ALA overlaps a wavelength band of an R component. For this reason, in a case in which a fluorescent image of fluorescence emitted from 5ALA is picked up, at least the output of an R component emitted from an RGB laser light source of the visible light source 1431, in light belonging to a visible light wavelength band and emitted from the visible light source 1431 of the light source apparatus 143, may be limited (for example, set to be in an off-state). Based on such a configuration and control, it is possible to observe a fluorescent image of fluorescence emitted from 5ALA using a visible light image generated on the basis of an image pickup result obtained by the image pickup element for picking up the visible light image 1051.

Subsequently, a description will be given focusing on a case in which laserphyrin is used as a fluorescent material. As depicted in FIG. 7, fluorescence emitted from laserphyrin belongs to a visible light wavelength band, and thus the fluorescence is incident into the camera head 105a and is then imaged on the image pickup element for picking up the visible light image 1051 through the color separation prism 201a and the short pass filter 211. For this reason, it is possible to observe a fluorescent image of fluorescence emitted from laserphyrin using a visible light image gener-
ated on the basis of an image pickup result obtained by the image pickup element for picking up the visible light image 1051.

Note that, in a case in which light in a wavelength band in the vicinity of an R component (for example, excitation light having a wavelength of 664 nm) is used as excitation light of a fluorescent material emitting fluorescence belonging to a visible light wavelength band such as 5ALA or laserphyrin, the notch filter 1055 blocking light belonging to an excitation wavelength of the fluorescent material may be mounted on the camera head 105a. Similarly, it is also possible to use excitation light having a wavelength of 405 nm as excitation light of laserphyrin. In this case, the notch filter 1055 blocking the excitation light (that is, light having a wavelength of 405 nm) may be mounted on the camera head 105a, or a long pass filter may be mounted on the camera head 105a instead of the notch filter 1055. With such a configuration, it is possible to prevent the incidence of the excitation light into the camera head 105a.

Spectral characteristics of the dichroic film 203, the notch filter 1055, the short pass filter 211, and the long pass filter 213 in the camera head 105a have been described above with reference to FIG. 7.

3.3. Configuration Example 2 of Two-Plate Type Camera Head

Figure 8:
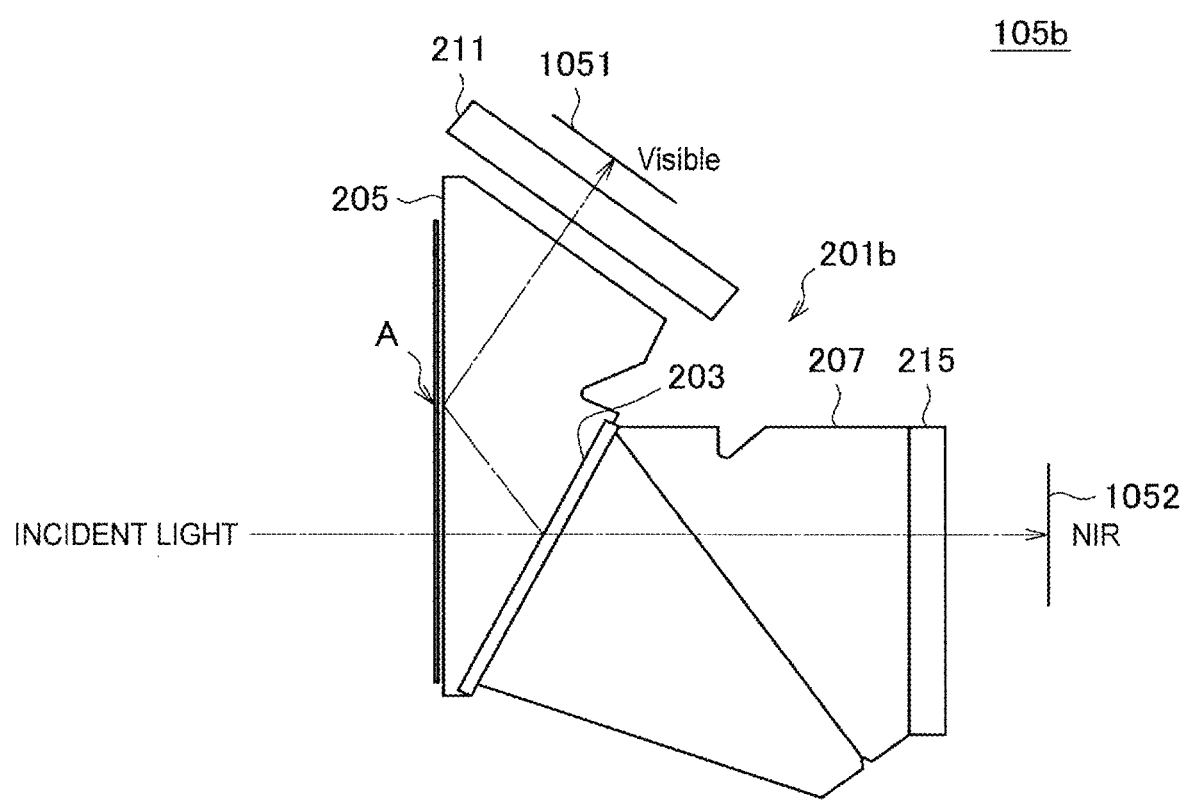
FIG. 8 is a schematic view depicting another example of a configuration of the camera head according to the embodiment.

Subsequently, as another example of a configuration of a camera head in the imaging system according to the present embodiment, reference will be made to FIG. 8 to describe as another example of a configuration of a two-plate type camera head, particularly, focusing on a configuration until incident light is imaged on an image pickup element through a branching optical system. FIG. 8 is a schematic view depicting another example of a configuration of a camera head according to the present embodiment. Note that, in the following description, the camera head 105 depicted in FIG. 8 may be referred to as "a camera head 105b" in a case in which the camera head 105 is expressly shown.

As depicted in FIG. 8, the camera head 105b includes a color separation prism 201b, an image pickup element for picking up the visible light image 1051, an image pickup element for picking up the near-infrared light image 1052, a short pass filter 211, and a bandpass filter 215. Note that the color separation prism 201b has the same configuration as that of the color separation prism 201a described with reference to FIG. 6, and is equivalent to an example of the branching optical system 201 depicted in FIG. 4. That is, the camera head 105b depicted in FIG. 8 is different from the camera head 105a described with reference to FIG. 6 in that the camera head 105b does not include a notch filter 1055 and includes the bandpass filter 215 instead of a long pass filter 213. Consequently, in the present description, a configuration of the camera head 105b will be described focusing on differences from the camera head 105a depicted in FIG. 6, and a detailed description of the same configuration as that of the camera head 105a will be omitted.

As described above, in the camera head 105b, the bandpass filter 215 is provided in a light path of light which is separated by the dichroic film 203 and is imaged on the image pickup element for picking up the near-infrared light image 1052. The bandpass filter 215 has a characteristic of transmitting light in at least a portion of a wavelength band of the predetermined wavelength band in a near-infrared wavelength band in accordance with a characteristic of a fluorescent material emitting fluorescence in the predetermined wavelength band and blocking light in the other wavelength bands. As a specific example, in a case of focusing on fluorescence emitted from ICG, the bandpass filter 215 may have a characteristic of transmitting light in a wavelength band (for example, a wavelength band of 820 nm to 850 nm) of approximately 820 nm which is a wavelength band of fluorescence emitted from ICG and blocking light in the other wavelength bands.

In this manner, in the camera head 105b, the bandpass filter 215 is provided at the front stage of the image pickup element for picking up the near-infrared light image 1052. For this reason, the camera head 105b can block excitation light of a fluorescent material such as ICG by the bandpass filter 215 even when the notch filter 1055 is not provided as in the camera head 105a in a case of focusing on fluorescence belonging to a near-infrared wavelength band and emitted from the fluorescent material. Note that the configuration of the camera head described in FIG. 8 is merely an example, and is not necessarily limited to the example depicted in FIG. 8. For example, the installation position of the image pickup element for picking up the visible light image 1051 and the installation position of the image pickup element for picking up the near-infrared light image 1052 may be reversed. In this case, for example, as the dichroic film 203, a dichroic film having a characteristic of transmitting light belonging to a visible light wavelength band and reflecting light belonging to a near-infrared wavelength band may be applied. That is, the characteristic of the dichroic film 203 may be appropriately changed in accordance with a relationship between the installation position of the image pickup element for picking up the visible light image 1051 and the installation position of the image pickup element for picking up the near-infrared light image 1052.

Figure 9:
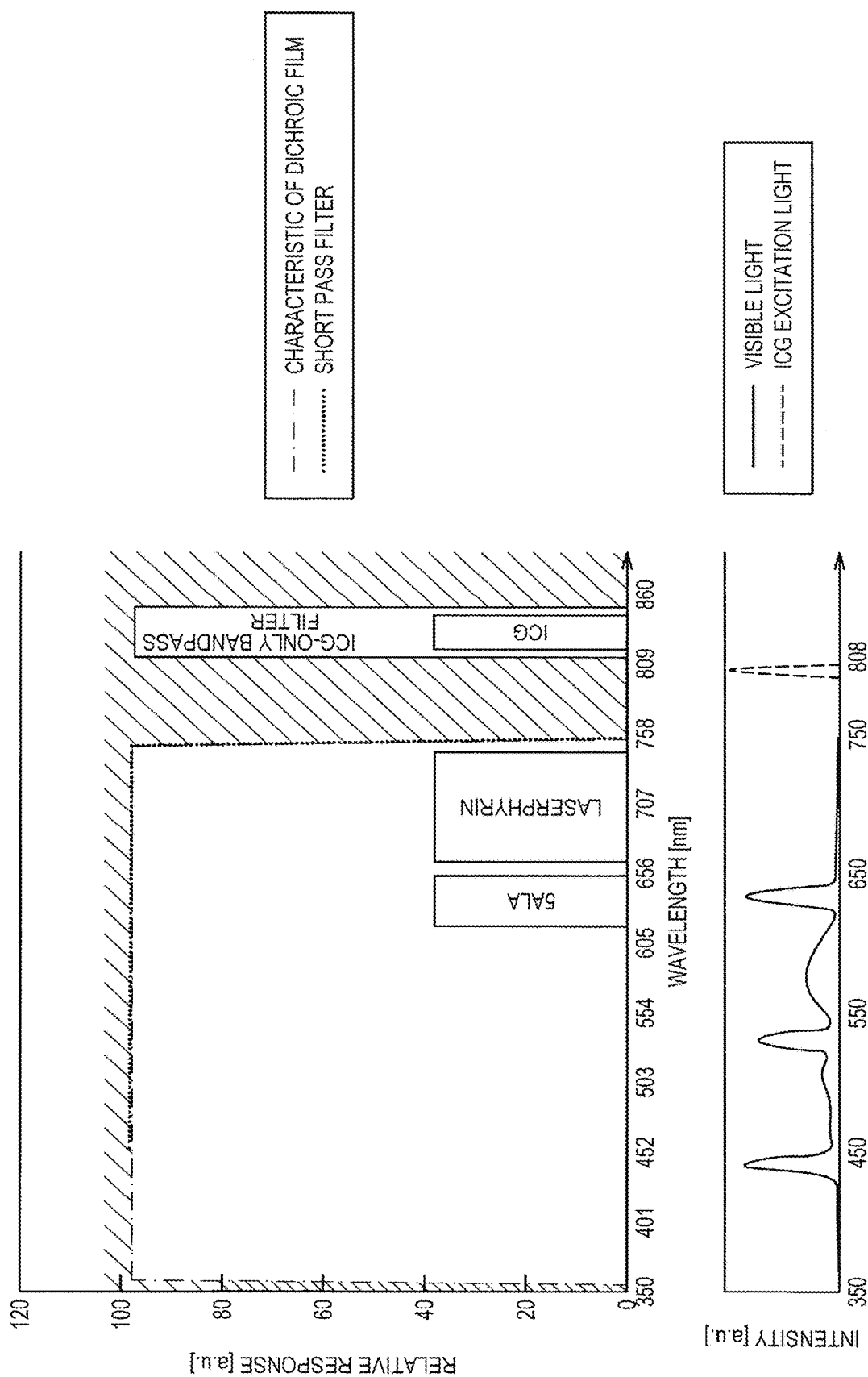
FIG. 9 is a view depicting another example of a relationship between spectral characteristics of the dichroic film and various filters according to the embodiment and a spectrum of light emitted from the light source apparatus.

Subsequently, spectral characteristics of the dichroic film 203, the short pass filter 211, and the bandpass filter 215 in the camera head 105b will be described with reference to FIG. 9. FIG. 9 is a view depicting another example of a relationship between spectral characteristics of a dichroic film and various filters according to the present embodiment and a spectrum of light emitted from a light source apparatus. For example, in the upper drawing of FIG. 9, spectral characteristics of the dichroic film 203, the short pass filter 211, and the bandpass filter 215a re schematically depicted. In addition, the lower drawing of FIG. 9 depicts a spectrum of light emitted from a light source apparatus according to the present embodiment. Note that the horizontal axis and the vertical axis in each of the upper drawing and the lower drawing in FIG. 9 are the same as those in the example depicted in FIG. 7. Further, in the example depicted in FIG. 9, the same light source apparatus as that in the example depicted in FIG. 7 is used. For this reason, the lower drawing of FIG. 9 is the same as the lower drawing of FIG. 7.

As described above, the camera head 105b depicted in FIG. 8 is different from the camera head 105a depicted in FIG. 6 in that the camera head 105b does not include the notch filter 1055 and includes the bandpass filter 215 instead of the long pass filter 213. In other words, the camera head 105b is the same as the case of the camera head 105a with regard to characteristics of the dichroic film 203 and the short pass filter 211. Consequently, in the present description, a description will be mainly given focusing on influence exerted due to the notch filter 1055 not being provided and a characteristic of the bandpass filter 215, and a detailed description of the same portion as that of the camera head 105a will be omitted.

In FIG. 9, regarding a band shown as a characteristic of an ICG-only bandpass filter, a wavelength band of each of light passing through the bandpass filter 215 depicted in FIG. 8 and light blocked by the bandpass filter 215 is schematically depicted. As described above, the bandpass filter 215 has a characteristic of transmitting light in at least a portion of a wavelength band of a predetermined wavelength band in a near-infrared wavelength band in accordance with a characteristic of a fluorescent material emitting fluorescence in the predetermined wavelength band and blocking light in the other wavelength bands. For this reason, in a case in which the bandpass filter 215 is provided on the assumption that ICG is used, the bandpass filter has a characteristic of transmitting light in a wavelength band (for example, a wavelength band of 820 nm to 850 nm) of approximately 820 nm which is a wavelength band of fluorescence emitted from ICG and blocking light in the other wavelength bands.

With the above-described configuration, in a case in which ICG is used as a fluorescent material, fluorescence emitted from ICG is incident into the camera head 105b and is then imaged on the image pickup element for picking up the near-infrared light image 1052 through the color separation prism 201b and the bandpass filter 215. Note that, as described above, the camera head 105b does not include a notch filter 1055. For this reason, in the camera head 105b, excitation light of ICG is incident into the camera head 105b and is guided to the inside of the color separation prism 201b to reach the bandpass filter 215. On the other hand, the bandpass filter 215 is provided at the front stage of the image pickup element for picking up the near-infrared light image 1052, so that excitation light of ICG is blocked by the bandpass filter 215. With such a configuration, it is possible to observe a fluorescent image of fluorescence emitted from ICG using a near-infrared light image generated on the basis of an image pickup result obtained by the image pickup element for picking up the near-infrared light image 1052.

Note that, since a case in which fluorescent images of 5ALA and laserphyrin are observed is the same as the case of the camera head 105a described with reference to FIG. 7, a detailed description thereof will be omitted. On the other hand, in a case in which light in a wavelength band in the vicinity of an R component (for example, excitation light having a wavelength of 664 nm) is used as excitation light of a fluorescent material emitting fluorescence belonging to a visible light wavelength band such as 5ALA or laserphyrin, the notch filter 1055 blocking light belonging to an excitation wavelength of the fluorescent material may be mounted on the camera head 105b. Similarly, also in a case in which excitation light having a wavelength of 405 nm is used as excitation light of laserphyrin, the notch filter 1055 blocking the excitation light (that is, light having a wavelength of 405 nm) may be mounted on the camera head 105b, or a long pass filter may be mounted on the camera head 105b instead of the notch filter 1055. With such a configuration, it is possible to prevent the incidence of the excitation light into the camera head 105b.

Spectral characteristics of the dichroic film 203, the short pass filter 211, and the bandpass filter 215 in the camera head 105b have been described above with reference to FIG. 9.

3.4. Configuration Example of Three-Plate Type Camera Head

Figure 10:
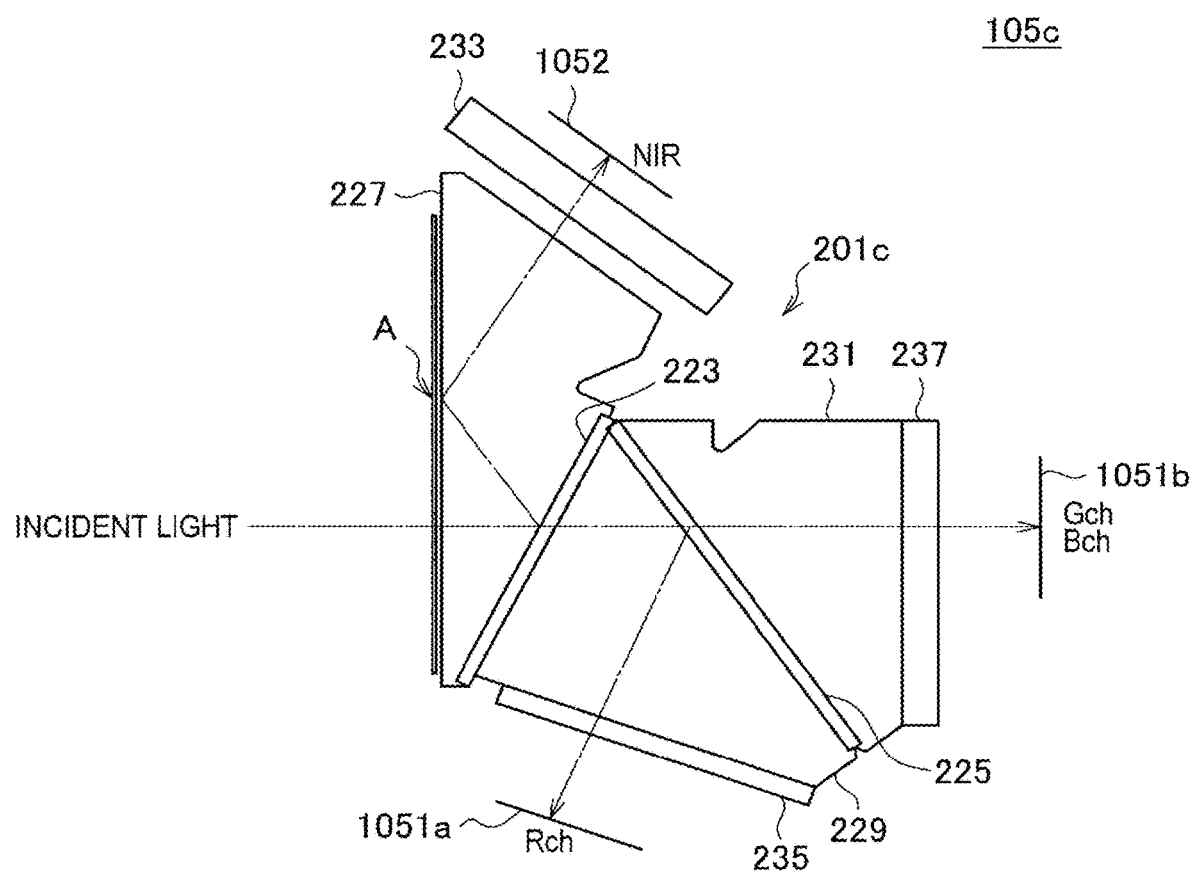
FIG. 10 is a schematic view depicting another example of a configuration of the camera head according to the embodiment.

Subsequently, as another example of a configuration of a camera head in the imaging system according to the present embodiment, a description will be given of an example of a configuration of a three-plate type camera head, particularly, focusing on a configuration until incident light is imaged on an image pickup element through a branching optical system. For example, FIG. 10 is a schematic view depicting another example of a configuration of a camera head according to the present embodiment. Note that, in the following description, the camera head 105 depicted in FIG. 10 may be referred to as "a camera head 105c" in a case in which the camera head 105 is expressly shown.

As illustrated in FIG. 10, the camera head 105c includes a color separation prism 201c, a first image pickup element for picking up the visible light image 1051a, a second image pickup element for picking up the visible light image 1051b, an image pickup element for picking up the near-infrared light image 1052, and bandpass filters 233, 235, and 237.

The color separation prism 201c is an optical member that separates incident light incident on the camera head 105c into light belonging to a visible light wavelength band and light belonging to a near-infrared wavelength band and then further separates the light belonging to a visible light wavelength band into light belonging to a long wavelength band including an R component and light belonging to a short wavelength band including a G component and a B component. Note that the color separation prism 201c is equivalent to another example of the branching optical system 201 depicted in FIG. 4. Specifically, dichroic films 223 and 225 are provided inside the color separation prism 201c. The dichroic film 223 is a dichroic film for separating light belonging to a visible light wavelength band and light belonging to a near-infrared wavelength band from each other. In addition, the dichroic film 225 is a dichroic film for separating the light belonging to a visible light wavelength band into light belonging to a wavelength band on a long wavelength side including an R component and light belonging to a wavelength band on a short wavelength side including a G component and a B component.

More specifically, as depicted in FIG. 10, the color separation prism 201c is a prism in which a first prism 227 and a second prism 229 are bonded to each other through the dichroic film 223 and a second prism 229 and a third prism 231 are bonded to each other through the dichroic film 225. That is, the dichroic film 223 is provided at an interface between the first prism 227 and the second prism 229. In addition, the dichroic film 225 is provided at an interface between the second prism 229 and the third prism 231.

The dichroic film 223 is an optical film that separates incident light incident on the color separation prism 201c and including light belonging to a visible light wavelength band and light belonging to a near-infrared wavelength band into light belonging to a visible light wavelength band and light belonging to a near-infrared wavelength band. Specifically, the dichroic film 223 has a characteristic of transmitting light belonging to a visible light wavelength band and reflecting light belonging to a near-infrared wavelength band.

In addition, the dichroic film 225 is an optical film that separates light belonging to a visible light wavelength band which has passed through the dichroic film 223 into light belonging to a wavelength band on a long wavelength side including an R component and light belonging to a wavelength band on a short wavelength side including a G component and a B component. Specifically, the dichroic film 225 has a characteristic of reflecting light belonging to a wavelength band on a long wavelength side including an R component and transmitting light belonging to a wavelength band on a short wavelength side including a G component and a B component. In addition, as another example, the dichroic film 225 may have a characteristic of transmitting light belonging to a wavelength band on a long wavelength side including an R component and reflecting light belonging to a wavelength band on a short wavelength side including a G component and a B component.

The first prism 227 is a prism functioning as a light path for near-infrared light on which light belonging to a visible light wavelength band and light belonging to a near-infrared wavelength band (that is, incident light) are incident and through which light belonging to a near-infrared wavelength band is guided. In addition, the second prism 229 is a prism functioning as a light path on which light belonging to a visible light wavelength band is incident and through which light belonging to a wavelength band on a long wavelength side including an R component in the visible light wavelength band is guided. In addition, the third prism 231 is a prism functioning as a light path through which light belonging to a wavelength band on a short wavelength side including a G component and a B component in the visible light wavelength band is guided.

Incident light incident on the first prism 227 travels straight inside the first prism 227 and is separated into light belonging to a visible light wavelength band and light belonging to a near-infrared wavelength band by the dichroic film 223 which is obliquely provided on the optical axis thereof.

The light belonging to a near-infrared wavelength band is reflected by the dichroic film 223 and is guided to the inside of the first prism 227. Here, the reflected and separated light belonging to a near-infrared wavelength band (that is, a near infrared ray) is totally reflected at a position A depicted in FIG. 10 only once and is transmitted to the outside of the first prism 227. Thereby, it is possible to bring an angle of a film formation surface of the dichroic film 223 with respect to the optical axis close to a right angle. Conversely, an installation angle on the optical axis of the dichroic film 223 according to the present embodiment is set such that a total reflection condition of visible rays at the position A is established. The dichroic film 223 is disposed in this manner, so that it is possible to suppress changes in spectral characteristics of the dichroic film 203 due to a difference in an incidence angle between an upper light beam and a lower light beam and to perform wavelength separation with a high level of accuracy even when a bright light beam having an F value is incident on the first prism 205.

Near infrared rays having passed through the first prism 227 are guided to the image pickup element for picking up the near-infrared light image 1052. In this case, the bandpass filter 233 is provided in a light path of light which is separated by the dichroic film 223 and is imaged on the image pickup element for picking up the near-infrared light image 1052. Note that the characteristic of the bandpass filter 233 is the same as that of the bandpass filter 215 described with reference to FIG. 8. That is, in a case of focusing on fluorescence emitted from ICG the bandpass filter 233 may have a characteristic of transmitting light in a wavelength band (for example, a wavelength band of 820 nm to 850 nm) of approximately 820 nm which is a wavelength band of fluorescence emitted from ICG and blocking light in the other wavelength bands. With such a configuration, it is possible to extract only noticed fluorescence in the light belonging to a near-infrared wavelength band separated by the dichroic film 214. Note that the long pass filter 213 described with reference to FIG. 6 may be provided instead of the bandpass filter 233. In this case, a notch filter 1055 may be mounted at the front stage of the color separation prism 201c.

In addition, light belonging to a visible light wavelength band which has passed through the dichroic film 223 is incident into the second prism 229. In addition, the light belonging to a visible light wavelength band travels straight inside the second prism 229 and is separated into light belonging to a wavelength band on a long wavelength side including an R component and light belonging to a wavelength band on a short wavelength side including a G component and a B component in the visible light wavelength band by the dichroic film 225 which is obliquely provided on the optical axis thereof.

The light belonging to the wavelength band on the long wavelength side including the R component is reflected by the dichroic film 225 and is guided to the inside of the second prism 229. An end surface (in other words, an emitting surface on a downstream side of the optical axis of the second prism 229) on a side opposite to the side where the dichroic film 225 is provided in the second prism 229 is provided so as to be perpendicular to the optical axis. For this reason, the light belonging to the wavelength band on the long wavelength side including the R component is transmitted to the outside of the second prism 229 while maintaining a state where the light is perpendicular to the emitting surface of the second prism 229.

The light belonging to the wavelength band on the long wavelength side including the R component and having passed through the second prism 229 is guided to the first image pickup element for picking up the visible light image 1051a. In this case, a bandpass filter 235 is provided in a light path of light which is separated by the dichroic film 225 and is imaged on the first image pickup element for picking up the visible light image 1051a. The bandpass filter 235 has a characteristic of transmitting light in a wavelength band on a long wavelength side including an R component and blocking light in the other wavelength bands in a visible light wavelength band. As a specific example, the bandpass filter 235 may have a characteristic of transmitting light in a wavelength band of 600 nm to 750 nm and blocking light in the other wavelength bands. With such a configuration, it is possible to exclude light in wavelength bands other than the wavelength band on a long wavelength side including an R component which is included in light separated by the dichroic film 225 (that is, light reflected by the dichroic film 225).

On the other hand, the light belonging to the wavelength band on the short wavelength side including the G component and the B component and having passed through the dichroic film 225 is incident on the third prism 231 and travels straight inside the third prism 231. An end surface (in other words, an emitting surface on a downstream side of the optical axis of the third prism 231) on a side opposite to the side where the dichroic film 225 is provided in the third prism 231 is provided so as to be perpendicular to the optical axis. For this reason, the light belonging to the wavelength band on the short wavelength side including the G component and the B component is transmitted to the outside of the third prism 231 while maintaining a state where the light is perpendicular to the emitting surface of the third prism 231.

The light belonging to the wavelength band on the short wavelength side including the G component and the B component and having passed through the third prism 231 is guided to the second image pickup element for picking up the visible light image 1051b. In this case, a bandpass filter 237 is provided in a light path of light which is separated by the dichroic film 225 and is imaged on the second image pickup element for picking up the visible light image 1051b. The bandpass filter 237 has a characteristic of transmitting light in a wavelength band on a short wavelength side including a B component and a G component and blocking light in the other wavelength bands in a visible light wavelength band. As a specific example, the bandpass filter 237 may have a characteristic of transmitting light in a wavelength band of 350 nm to 600 nm and blocking light in the other wavelength bands. With such a configuration, it is possible to exclude light in wavelength bands other than the wavelength band on a short wavelength side including a B component and a G component which is included in light separated by the dichroic film 225 (that is, light having passed through the dichroic film 225).

Note that a material of the color separation prism 201c according to the present embodiment is not particularly limited, and it is possible to appropriately use known optical glass or optical crystal in accordance with a wavelength of light guided to the inside of the color separation prism 201c.

The first image pickup element for picking up the visible light image 1051a is provided at the succeeding stage of the color separation prism 201c and the bandpass filter 235. That is, light, separated by the color separation prism 201c and having passed through the bandpass filter 235, in a wavelength band on a long wavelength side including an R component in a visible light wavelength band is imaged on the first image pickup element for picking up the visible light image 1051a. Note that fluorescence emitted from 5ALA or laserphyrin belongs to a wavelength band on a long wavelength side including an R component in a visible light wavelength band. That is, the fluorescence emitted from 5ALA or laserphyrin is also imaged on the first image pickup element for picking up the visible light image 1051a. From such a characteristic, it is preferable that an image pickup element having higher sensitivity be applied as the first image pickup element for picking up the visible light image 1051a, and for example, an image pickup element, such as a CCD or a CMOS, which is not provided with a color filter and the like may be applied.

The second image pickup element for picking up the visible light image 1051b is provided at the succeeding stage of the color separation prism 201c and the bandpass filter 237. That is, light, separated by the color separation prism 201c and having passed through the bandpass filter 237, in a wavelength band on a short wavelength side including a G component and a B component in a visible light wavelength band is imaged on the second image pickup element for picking up the visible light image 1051b. As the second image pickup element for picking up the visible light image 1051b, for example, an image pickup element, such as a CCD or a CMOS, which includes an RGB color filter can be applied.

The image pickup element for picking up the near-infrared light image 1052 is provided at the succeeding stage of the color separation prism 201c and the bandpass filter 233. That is, light separated by the color separation prism 201c and having passed through the bandpass filter 233, that is, light in at least a portion of a wavelength band of fluorescence emitted from a predetermined fluorescent material (for example, ICG) is imaged on the image pickup element for picking up the near-infrared light image 1052. From such a characteristic, it is preferable that an image pickup element having higher sensitivity be applied as the image pickup element for picking up the near-infrared light image 1052, and for example, an image pickup element, such as a CCD or a CMOS, which is not provided with a color filter and the like may be applied.

As another example of a configuration of a camera head in the imaging system according to the present embodiment, reference has been made to FIG. 10 above to describe an example of a configuration of a three-plate type camera head, particularly, focusing on a configuration until incident light is imaged on an image pickup element through a branching optical system.

Figure 11:
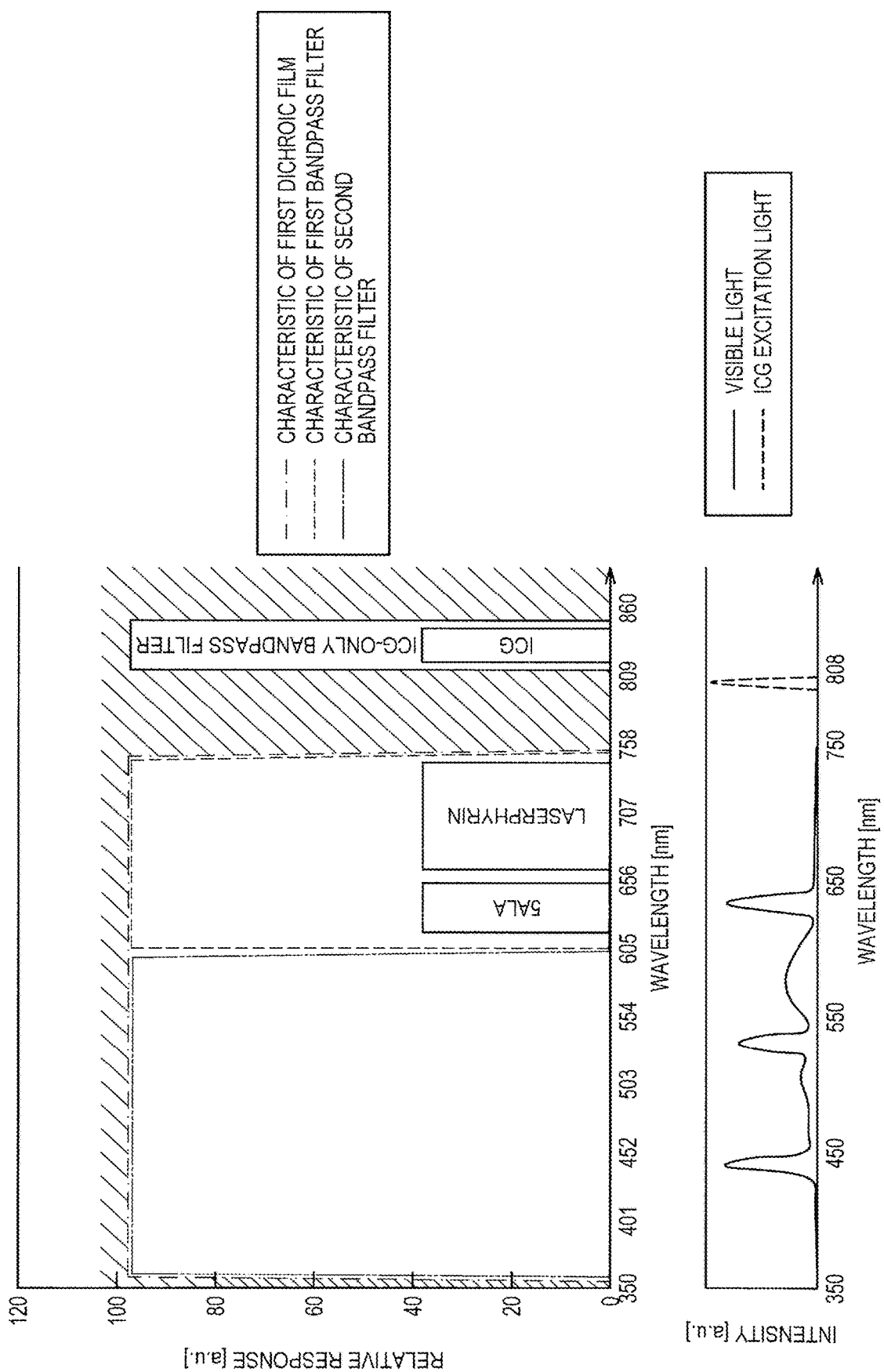
FIG. 11 is a view depicting another example of a relationship between spectral characteristics of the dichroic film and various filters according to the embodiment and a spectrum of light emitted from the light source apparatus.

Subsequently, spectral characteristics of each of the dichroic films 223 and 225 and the bandpass filters 233, 235, and 237 in the camera head 105*c* will be described with reference to FIG. 11. FIG. 11 is a view depicting another example of a relationship between spectral characteristics of a dichroic film and various filters according to the present embodiment and a spectrum of light emitted from a light source apparatus. For example, in the upper drawing of FIG. 11, spectral characteristics of each of the dichroic film 223 and the bandpass filters 233, 235, and 237 are schematically depicted. Note that, in the upper drawing of FIG. 11, spectral characteristics of the dichroic film 225 are not depicted in order to avoid complication of the drawing. In addition, the lower drawing of FIG. 11 depicts a spectrum of light emitted from the light source apparatus according to the present embodiment. Note that the horizontal axis and the vertical axis in each of the upper drawing and the lower drawing in FIG. 11 are the same as those in the example depicted in FIG. 7. Further, in the example depicted in FIG. 11, the same light source apparatus as that in the example depicted in FIG. 7 is used. For this reason, the lower drawing in FIG. 11 is the same as the lower drawing in FIG. 7.

In FIG. 11, a graph plotted as dichroic film characteristics schematically depicts a wavelength band of each of light reflected by the dichroic film 223 depicted in FIG. 10 and light passing through the dichroic film 223. Specifically, the inner side of the graph plotted as dichroic film characteristics is equivalent to a component passing through the dichroic film 223, and the outer side of the graph is equivalent to a component reflected by the dichroic film 223. That is, the dichroic film 223 has a characteristic of transmitting most (for example, equal to or greater than 90%) of light in a wavelength band of 350 nm to 750 nm and reflecting most (for example, equal to or greater than 90%) of light in a wavelength band exceeding 750 nm.

In addition, as described above, the dichroic film 225 reflects light belonging to a wavelength band on a long wavelength side including an R component and transmits light belonging to a wavelength band on a short wavelength side including a G component and a B component in light belonging to a visible light wavelength band. As a more specific example, the dichroic film 225 may have a characteristic of reflecting most (for example, equal to or greater than 90%) of light in a wavelength band of 600 nm to 750 nm and transmitting most (for example, equal to or greater than 90%) of light in a wavelength band of 350 nm to 600 nm in light in a wavelength band of 350 nm to 750 nm.

Further, in FIG. 11, a graph plotted as first bandpass filter characteristics schematically depicts a wavelength band of each of light passing through the bandpass filter 235 depicted in FIG. 10 and light blocked by the bandpass filter 235. As described above, for example, the bandpass filter 235 transmits light in a wavelength band of 600 nm to 750 nm and blocks light in the other wavelength bands. With such a configuration, for example, it is possible to image light in a wavelength band on a long wavelength side including an R component, in light belonging to a visible light wavelength band and emitted from the visible light source 1431 of the light source apparatus 143 and guided to the inside of the camera head 105*c*, on the first image pickup element for picking up the visible light image 1051*a*.

Further, in FIG. 11, a graph plotted as second bandpass filter characteristics schematically depicts a wavelength band of each of light passing through the bandpass filter 237 depicted in FIG. 10 and light blocked by the bandpass filter 237. As described above, for example, the bandpass filter 237 transmits light in a wavelength band of 350 nm to 600 nm and blocks light in the other wavelength bands. With such a configuration, for example, it is possible to image light in a wavelength band on a short wavelength side including a G component and a B component, in light belonging to a visible light wavelength band and emitted from the visible light source 1431 of the light source apparatus 143 and guided to the inside of the camera head 105*c*, on the second image pickup element for picking up the visible light image 1051*b*.

Further, in FIG. 11, regarding a band shown as a characteristic of an ICG-only bandpass filter, a wavelength band of each of light passing through the bandpass filter 233 depicted in FIG. 8 and light blocked by the bandpass filter 233 is schematically depicted. As described above, the bandpass filter 233 has a characteristic of transmitting light in at least a portion of a wavelength band of a predetermined wavelength band in a near-infrared wavelength band in accordance with a characteristic of a fluorescent material emitting fluorescence in the predetermined wavelength band and blocking light in the other wavelength bands. For this reason, in a case in which the bandpass filter 233 is provided on the assumption that ICG is used, the bandpass filter has a characteristic of transmitting light in a wavelength band (for example, a wavelength band of 820 nm to 850 nm) of approximately 820 nm which is a wavelength band of fluorescence emitted from ICG and blocking light in the other wavelength bands.

Based on the above-described configuration, the camera head 105*c* can pick up, for example, a fluorescent image of fluorescence belonging to a near-infrared wavelength band and emitted from a fluorescent material such as ICG or a fluorescent image of fluorescence belonging to a visible light wavelength band and emitted from a fluorescent material such as 5ALA and laserphyrin.

As a specific example, a description will be given focusing on a case in which ICG is used as a fluorescent material. Since fluorescence emitted from ICG belongs to a near-infrared wavelength band, the fluorescence is incident into the camera head 105*c* and is then imaged on the image pickup element for picking up the near-infrared light image 1052 through the color separation prism 201*c* and the bandpass filter 233. Note that the camera head 105*c* does not include a notch filter 1055, similar to the camera head 105*b* described with reference to FIG. 8. For this reason, in the camera head 105*c*, excitation light of ICG is incident into the camera head 105*c* and is guided to the inside of the color separation prism 201*c* to reach the bandpass filter 233. On the other hand, the bandpass filter 233 is provided at the front stage of the image pickup element for picking up the near-infrared light image 1052, so that excitation light of ICG is blocked by the bandpass filter 233. With such a configuration, it is possible to observe a fluorescent image of fluorescence emitted from ICG using a near-infrared light image generated on the basis of an image pickup result obtained by the image pickup element for picking up the near-infrared light image 1052.

Subsequently, a description will be given focusing on a case in which 5ALA is used as a fluorescent material. As depicted in FIG. 11, fluorescence emitted from 5ALA belongs to a wavelength band on a long wavelength side including an R component in a visible light wavelength band. For this reason, fluorescence emitted from 5ALA is incident into the camera head 105*c* and is then imaged on the first image pickup element for picking up the visible light image 1051a through the color separation prism 201a and the bandpass filter 235. In addition, in a case in which a fluorescent image of fluorescence emitted from 5ALA is picked up, at least the output of an R component emitted from an RGB laser light source of the visible light source 1431, in light belonging to a visible light wavelength band and emitted from the visible light source 1431 of the light source apparatus 143, may be limited (for example, set to be in an off-state). Based on such a configuration and control, it is possible to observe a fluorescent image of fluorescence emitted from 5ALA using a visible light image generated on the basis of an image pickup result obtained by the first image pickup element for picking up the visible light image 1051a.

Subsequently, a description will be given focusing on a case in which laserphyrin is used as a fluorescent material. As depicted in FIG. 11, fluorescence emitted from laserphyrin belongs to a wavelength band on a long wavelength side including an R component in a visible light wavelength band. For this reason, fluorescence emitted from laserphyrin is incident into the camera head 105c and is then imaged on the first image pickup element for picking up the visible light image 1051a through the color separation prism 201a and the bandpass filter 235. For this reason, it is possible to observe a fluorescent image of fluorescence emitted from laserphyrin using a visible light image generated on the basis of an image pickup result obtained by the first image pickup element for picking up the visible light image 1051a.

Note that, in a case in which light in a wavelength band in the vicinity of an R component (for example, excitation light having a wavelength of 664 nm) is used as excitation light of a fluorescent material emitting fluorescence belonging to a visible light wavelength band such as 5ALA or laserphyrin, the notch filter 1055 blocking light belonging to an excitation wavelength of the fluorescent material may be mounted on the camera head 105c. Similarly, also in a case in which excitation light having a wavelength of 405 nm is used as excitation light of laserphyrin, the notch filter 1055 blocking the excitation light (that is, light having a wavelength of 405 nm) may be mounted on the camera head 105c or a long pass filter may be mounted on the camera head 105c instead of the notch filter 1055. With such a configuration, it is possible to prevent the incidence of the excitation light into the camera head 105c.

Subsequently, a case in which a visible light image of an image pickup target is observed using the camera head 105c will be described. As described above, in the camera head 105c, light belonging to a wavelength band on a long wavelength side including an R component in light belonging to a visible light wavelength band is imaged on the first image pickup element for picking up the visible light image 1051a, and light belonging to a wavelength band on a short wavelength side including a G component and a B component is imaged on the second image pickup element for picking up the visible light image 1051b. For this reason, for example, the camera head 105c may generate a visible light image of an image pickup target by composing images based on image pickup results respectively obtained by the first image pickup element for picking up the visible light image 1051a and the second image pickup element for picking up the visible light image 1051b.

As described above, in the three-plate type camera head 105c, a light belonging to a visible light wavelength band is separated into light belonging to a wavelength band on a long wavelength side including an R component and light belonging to a wavelength band on a short wavelength side including a G component and a B component, and the separated light beams are respectively imaged on different image pickup elements. With such a configuration, the camera head 105c can superimpose a fluorescent image of fluorescence emitted from a fluorescent material such as 5ALA or laserphyrin on, for example, an image of an image pickup target based on the light belonging to the wavelength band on the short wavelength side including the G component and the B component. In addition, the camera head 105c can perform different image processing on each of the fluorescent image of fluorescence emitted from the fluorescent material such as 5ALA or laserphyrin and the image of the image pickup target based on the light belonging to the wavelength band on the short wavelength side including the G component and the B component.

Spectral characteristics of the dichroic films 223 and 225 and the bandpass filters 233, 235, and 237 in the camera head 105c have been described above with reference to FIG. 11.

3.5. Operational Effects

Figure 12:
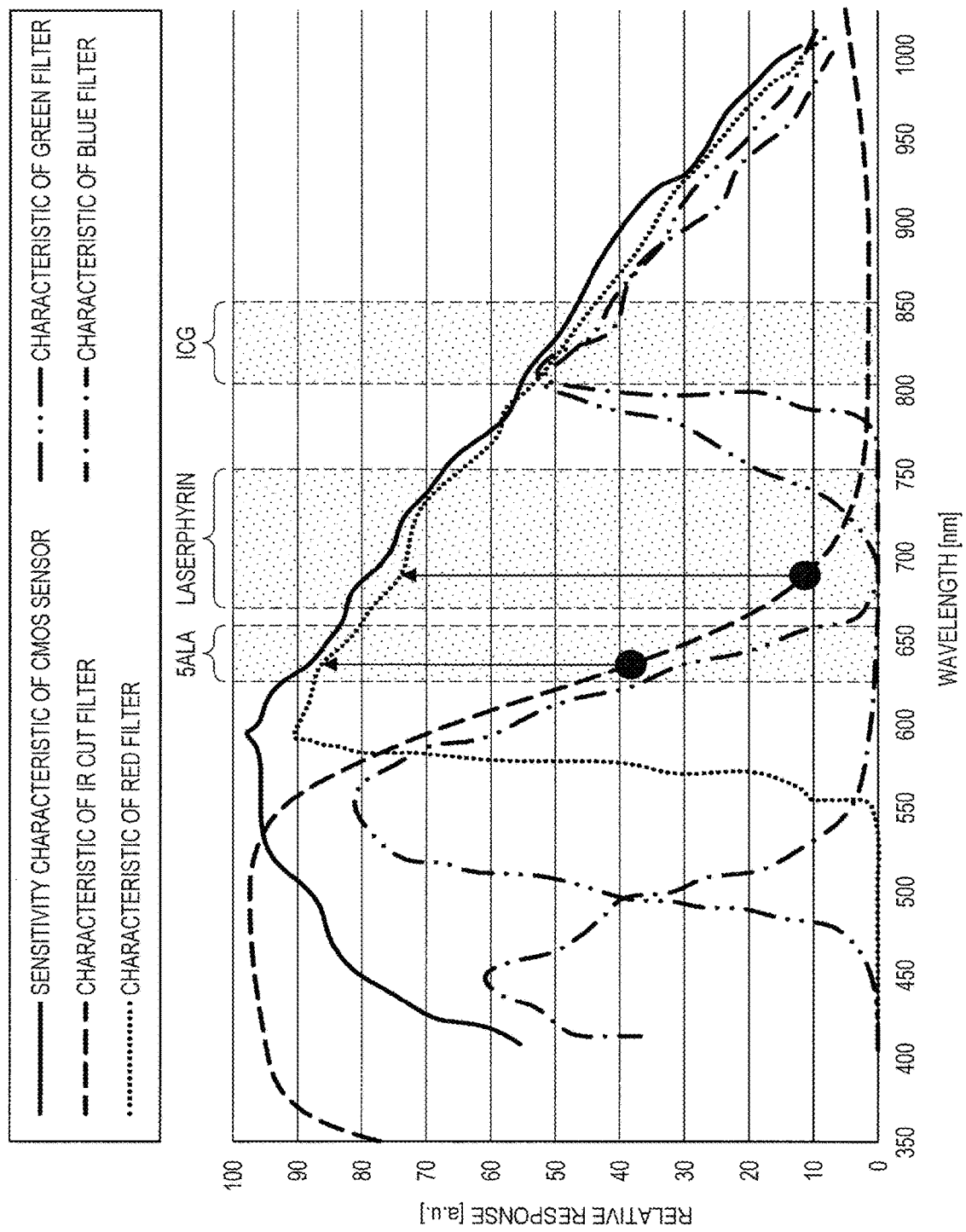
FIG. 12 is a view depicting characteristics of the camera head according to the embodiment.

Subsequently, operational effects obtained by applying the imaging system according to the present embodiment will be described with reference to FIG. 12. FIG. 12 is a view depicting characteristics of a camera head according to the present embodiment, and depicts an example of sensitivity characteristics for each wavelength of an image pickup element applied to a camera head such as an endoscopic image pickup system and spectral transmission characteristics of a color filter applied to the image pickup element. In FIG. 12, the horizontal axis represents a wavelength, and the vertical axis represents sensitivity characteristics for each wavelength of the image pickup element and spectral transmission characteristics of various filters by a relative value (%). Note that, in the example depicted in FIG. 12, an example of sensitivity characteristics for each wavelength of a so-called CMOS sensor is depicted as sensitivity characteristics of the image pickup element. Further, in the example depicted in FIG. 12, an example of spectral transmission characteristics is depicted for each of a red filter, a green filter, and a blue filter as characteristics of a color filter.

In addition, among the existing camera heads, in a camera head capable of picking up a visible light image of an image pickup target, an IR cut filter that cuts infrared light may be provided at the front stage of an image pickup element on which light belonging to a visible light wavelength band is imaged, in order to improve color reproducibility of the visible light image. Based on these points, in order to make it easier to understand operational effects obtained by applying the imaging system according to the present embodiment, an example of spectral transmission characteristics of an IR cut filter is also presented as a reference in the example depicted in FIG. 12. Note that, for example, C5000 manufactured by HOYA Corporation or the like is used as the IR cut filter.

As described above, among fluorescent materials emitting fluorescence in a visible light wavelength band, 5ALA emits fluorescence in a visible light region of approximately 635 nm (particularly, a wavelength band of an R component). In addition, laserphyrin emits fluorescence in the vicinity of a wavelength band of 670 nm to 730 nm, that is, fluorescence in a visible light region (particularly, in the vicinity of a near-infrared region) to a near-infrared region. For this reason, in a case in which a fluorescent image of fluorescence emitted from 5ALA or laserphyrin is picked up, the fluorescent image is picked up by an image pickup element on which light belonging to a visible light wavelength band is imaged.

On the other hand, as depicted in FIG. 12, an IR cut filter generally tends to have transmittance decreasing in a wavelength band on a long wavelength side including an R component in a visible light wavelength band. For this reason, for example, transmittance of an IR cut filter decreases to approximately 40% at a wavelength position of approximately 635 nm which is a wavelength of fluorescence emitted from 5ALA. In addition, transmittance of an IR cut filter decreases to approximately 20% to approximately several % at a wavelength position of 670 nm to 730 nm which is a wavelength of fluorescence emitted from laserphyrin. Fluorescence emitted from each fluorescent material tends to have lower light intensity than that of other light such as visible rays reflected by an image pickup target and incident into a camera head and excitation light of the fluorescent material. For this reason, in a case of a configuration in which an IR cut filter is provided at the front stage of an image pickup element, it is difficult to clearly pick up a fluorescent image of fluorescence belonging to a visible light wavelength band and emitted from 5ALA or laserphyrin.

On the other hand, in a camera head according to the present embodiment, an IR cut filter is not provided at the front stage of an image pickup element picking up an image of light belonging to a visible light wavelength band, for example, as described above with reference to FIGS. 6 to 11, and a short pass filter or a bandpass filter is provided instead. That is, in the camera head according to the present embodiment, it is possible to prevent the occurrence of a situation where fluorescence emitted from 5ALA or laserphyrin and guided to the image pickup element is limited by the IR cut filter when the fluorescence is imaged on the image pickup element. For this reason, according to the camera head of the present embodiment, since it is possible to more utilize performance of the camera head (particularly, the image pickup element) also in a case in which a fluorescent image of fluorescence belonging to a visible light wavelength band is picked up, it is possible to pick up a clearer fluorescent image.

An example of operational effects obtained by applying the imaging system according to the present embodiment has been described above with reference to FIG. 12.

4. EXAMPLE OF HARDWARE CONFIGURATION

Figure 13:
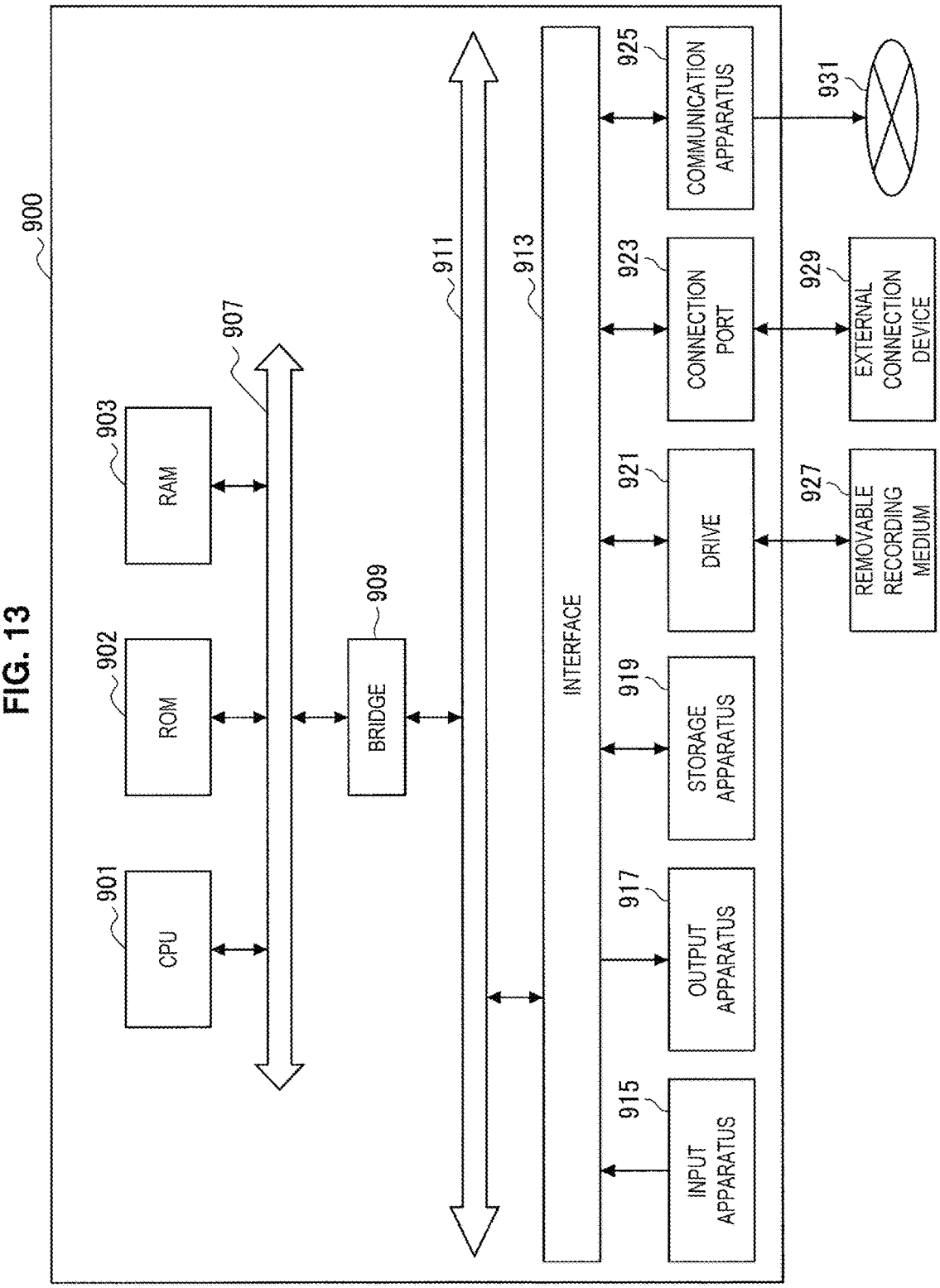
FIG. 13 is a functional block diagram depicting a configuration example of a hardware configuration of an information processing apparatus constituting the endoscopic image pickup system according to the embodiment of the present disclosure.

Subsequently, an example of a hardware configuration of a so-called information processing apparatus executing various processes like a CCU in the above-described endoscopic image pickup system (that is, the endoscopic surgery system) will be described in detail with reference to FIG. 13. FIG. 13 is a functional block diagram depicting a configuration example of a hardware configuration of an information processing apparatus constituting the endoscopic image pickup system according to the embodiment of the present disclosure.

The information processing apparatus 900 configuring the endoscopic image pickup system according to the present embodiment mainly includes a CPU 901, a ROM 903, and a RAM 905. The information processing apparatus 900 further includes a host bus 907, a bridge 909, an external bus 911, an interface 913, an input apparatus 915, an output apparatus 917, a storage apparatus 919, a drive 921, a connection port 923, and a communication apparatus 925.

The CPU 901 functions as an arithmetic processing apparatus and a control apparatus, and controls all or some operations of the information processing apparatus 900 according to various kinds of programs recorded in the ROM 903, the RAM 905, the storage apparatus 919, or a removable recording medium 927. The ROM 903 stores a program, an operation parameter, or the like used by the CPU 901. The RAM 905 primarily stores a program used by the CPU 901, a parameter that appropriately changes in execution of a program, or the like. The above-mentioned components are connected with one another by the host bus 907 including an internal bus such as a CPU bus.

The host bus 907 is connected to the external bus 911 such as a peripheral component interconnect/interface (PCI) bus through the bridge 909. Further, the input apparatus 915, the output apparatus 917, the storage apparatus 919, the drive 921, the connection port 923, and the communication apparatus 925 are connected to the external bus 911 via the interface 913.

The input apparatus 915 is an operating means used by the user such as a mouse, a keyboard, a touch panel, a button, a switch, a lever, or a pedal. For example, the input apparatus 915 may be a remote control means (a so-called remote controller) using infrared light or any other radio waves, and may be an external connection device 929 such as a mobile telephone or a PDA corresponding to an operation of the information processing apparatus 900. Further, for example, the input apparatus 915 includes an input control circuit that generates an input signal on the basis of information input by the user using the operating means, and outputs the input signal to the CPU 901. The user of the information processing apparatus 900 can input various kinds of data to the information processing apparatus 900 or instruct the information processing apparatus 900 to perform a processing operation by operating the input apparatus 915.

The output apparatus 917 includes an apparatus capable of visually or acoustically notifying the user of the acquired information. As such an apparatus, there are a display apparatus such as a CRT display apparatus, a liquid crystal display apparatus, a plasma display apparatus, an EL display apparatus or a lamp, an audio output apparatus such as a speaker or a headphone, a printer apparatus, and the like. For example, the output apparatus 917 outputs a result obtained by various kinds of processes performed by the information processing apparatus 900. Specifically, the display apparatus displays a result obtained by various kinds of processes performed by the information processing apparatus 900 in the form of text or an image. Meanwhile, the audio output apparatus converts an audio signal including reproduced audio data, acoustic data, or the like into an analogue signal, and outputs the analogue signal.

The storage apparatus 919 is a data storage apparatus configured as an exemplary storage section of the information processing apparatus 900. For example, the storage apparatus 919 includes a magnetic storage section device such as a hard disk drive (HDD), a semiconductor storage device, an optical storage device, a magneto optical storage device, or the like. The storage apparatus 919 stores a program executed by the CPU 901, various kinds of data, and the like.

The drive 921 is a recording medium reader/writer, and is equipped in or attached to the information processing apparatus 900. The drive 921 reads information stored in the removable recording medium 927 mounted thereon such as a magnetic disk, an optical disc, a magneto optical disc, or a semiconductor memory, and outputs the read information to the RAM 905. Further, the drive 921 can write a record in the removable recording medium 927 mounted thereon such as a magnetic disk, an optical disk, a magneto optical disk, or a semiconductor memory. For example, the removable recording medium 927 is a DVD medium, an HD-DVD medium, a Blu-ray (a registered trademark) medium, or the like. Further, the removable recording medium 927 may be a Compact Flash (CF) (a registered trademark), a flash memory, a Secure Digital (SD) memory card, or the like. Furthermore, for example, the removable recording medium 927 may be an integrated circuit (IC) card equipped with a non-contact type IC chip, an electronic device, or the like.

The connection port 923 is a port for connecting a device directly with the information processing apparatus 900. As an example of the connection port 923, there are a Universal Serial Bus (USB) port, an IEEE1394 port, a Small Computer System Interface (SCSI) port, and the like. As another example of the connection port 923, there are an RS-232C port, an optical audio terminal, a High-Definition Multimedia Interface (HDMI) (a registered trademark), and the like. As the external connection device 929 is connected to the connection port 923, the information processing apparatus 900 acquires various kinds of data directly from the external connection device 929 or provides various kinds of data to the external connection device 929.

For example, the communication apparatus 925 is a communication interface including a communication device or the like used for a connection with a communication network (network) 931. For example, the communication apparatus 925 is a communication card for a wired or wireless local area network (LAN), Bluetooth (a registered trademark), or wireless USB (WUSB). Further, the communication apparatus 925 may be an optical communication router, an asymmetric digital subscriber line (ADSL) router, various kinds of communication modems, or the like. For example, the communication apparatus 925 can transmit or receive a signal to or from the Internet or another communication apparatus, for example, according to a certain protocol such as TCP/IP. Further, the communication network 931 connected to the communication apparatus 925 includes a network connected in a wired or wireless manner, and may be, for example, the Internet, a domestic LAN, infrared ray communication, radio wave communication, satellite communication, or the like.

The hardware configuration capable of implementing the functions of the information processing apparatus 900 configuring the endoscopic image pickup system according to an embodiment of the present disclosure has been described above. Each of the above components may be configured using a versatile member, and may be configured by hardware specialized for the function of each component. Thus, the hardware configuration to be used may be appropriately changed according to a technology level when the present embodiment is carried out. Note that, although not depicted in FIG. 13, it obviously includes various kinds of components corresponding to the information processing apparatus 900 configuring the endoscopic image pickup system.

Note that it is possible to create a computer program for implementing the functions of the information processing apparatus 900 configuring the endoscopic image pickup system according to the present embodiment, and install the computer program in a personal computer or the like. Furthermore, it is possible to provide a computer readable recording medium storing the computer program as well. Examples of the recording medium include a magnetic disk, an optical disc, a magneto optical disc, and a flash memory. Further, for example, the computer program may be delivered via a network without using the recording medium. In addition, the number of computers causing the computer program to be executed is not particularly limited. For example, the computer program may be executed in cooperation of a plurality of computers (for example, a plurality of servers or the like).

5. APPLICATION EXAMPLE

Subsequently, as an application example of the imaging system according to the embodiment of the present disclosure, an example of a case in which the imaging system is configured as a microscope imaging system including a microscope unit will be described.

Figure 14:
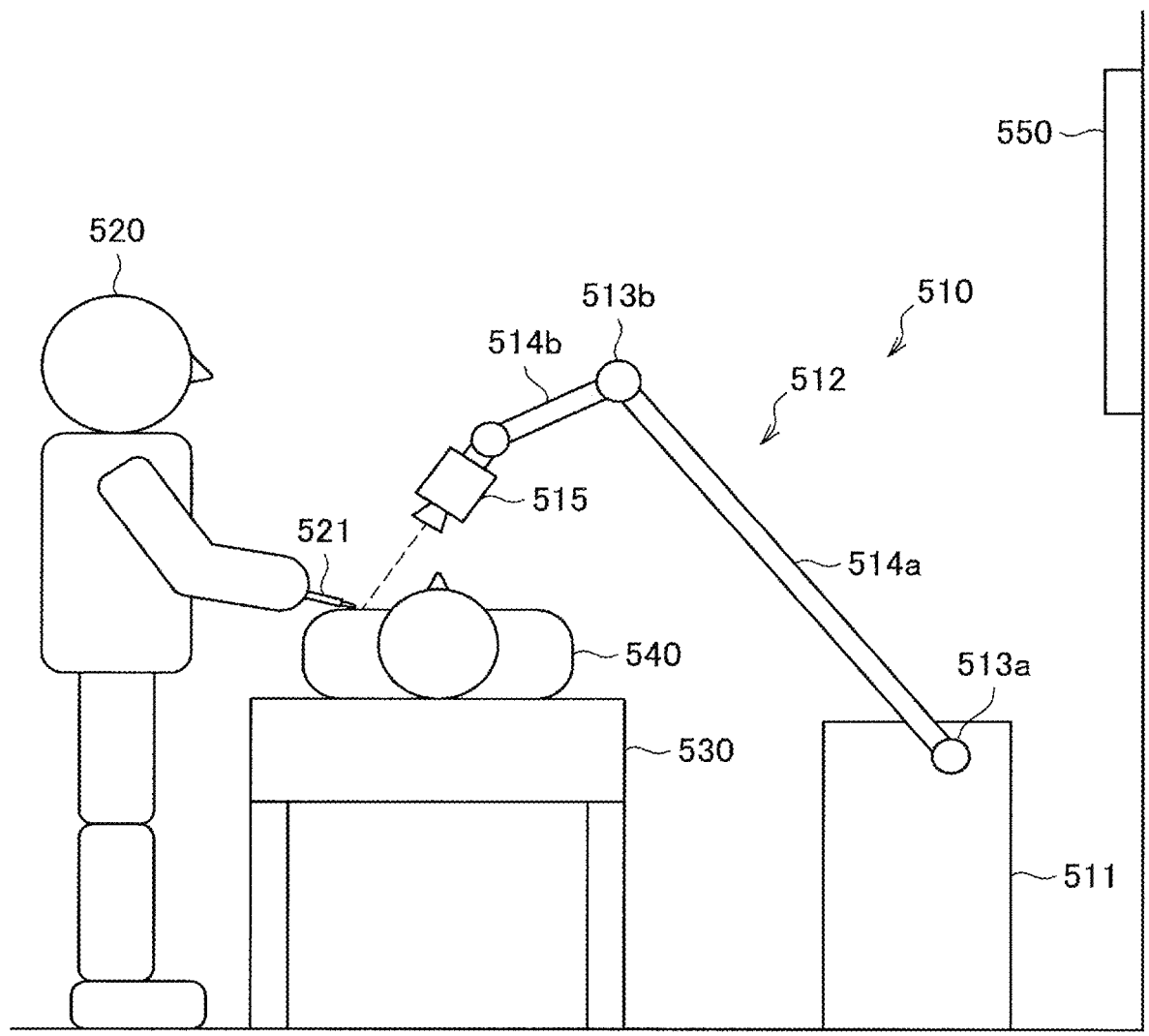
FIG. 14 is a view depicting an application example of the imaging system according to the embodiment of the present disclosure.

For example, FIG. 14 is a view depicting an application example of the imaging system according to the embodiment of the present disclosure, and depicts an example of a schematic configuration of a microscope imaging system. Specifically, FIG. 14 depicts an example of a case in which a video microscope apparatus for surgery including an arm as an application example of a case in which the microscope imaging system according to the embodiment of the present disclosure is used.

For example, FIG. 14 schematically depicts a state of a medical treatment using the video microscope apparatus for surgery. Specifically, referring to FIG. 14, a state where a medical doctor who is a surgeon (user) 520 performs surgery on a medical treatment target (patient) 540 on a medical treatment table 530 using an appliance for surgery 521 such as a scalpel, tweezers, or forceps is depicted. Note that, in the following description, it is assumed that medical treatment generically refers to various medical treatment, such as surgery or examination, which is to be performed on a patient who is the medical treatment target 540 by the medical doctor who is the user 520. Further, in the example depicted in FIG. 14, a state of surgery is depicted as an example of medical treatment, but the medical treatment used by the video microscope apparatus for surgery 510 is not limited to surgery and may be various medical treatment.

The video microscope apparatus for surgery 510 is provided beside the medical treatment table 530. The video microscope apparatus for surgery 510 includes a base unit 511 serving as a base, an arm unit 512 extending from the base unit 511, and an image pickup unit 515 connected to a distal end of the arm unit 512 as a distal end unit. The arm unit 512 includes a plurality of joint portions 513*a*, 513*b*, and 513*c*, a plurality of links 514*a* and 514*b* connected to each other by the joint portions 513*a* and 513*b*, and the image pickup unit 515 provided at the distal end of the arm unit 512. In the example depicted in FIG. 14, for simplification, the arm unit 512 includes three joint portions 513*a* to 513*c* and two links 514*a* and 514*b*. However, actually, in consideration of the degree of freedom of the positions and postures of the arm unit 512 and the image pickup unit 515, the number and shapes of the joint portions 513*a* to 513*c* and the links 514*a* and 514*b*, the direction of driving axes of the joint portions 513*a* to 513*c*, and the like may be appropriately set so as to realize a desired degree of freedom.

The joint portions 513*a* to 513*c* have a function of rotatably connecting the links 514*a* and 514*b* to each other, and the driving of the arm unit 512 is controlled by driving the rotation of the joint portions 513*a* to 513*c*. Here, in the following description, the position of each constituent member of the video microscope apparatus for surgery 510 means a position (coordinates) in a space defined for driving control, and the posture of each constituent member means a direction (angle) with respect to any axis in a space defined for driving control. Further, in the following description, the driving (or driving control) of the arm unit 512 refers to a change (control of a change) in the position and posture of each constituent member of the arm unit 512 by performing the driving (or driving control) of the joint portions 513a to 513c and performing the driving (or driving control) of the joint portions 513a to 513c.

The image pickup unit 515 is connected to the distal end of the arm unit 512 as a distal end unit. The image pickup unit 515 is a unit that acquires an image of an image pickup target, and is, for example, a camera capable of picking up a moving image and a still image. As depicted in FIG. 14, the postures and positions of the arm unit 512 and the image pickup unit 515 are controlled by the video microscope apparatus for surgery 510 so that the image pickup unit 515 provided at the distal end of the arm unit 512 picks up an image of a state of a medical treatment region of the medical treatment target 540. Note that a configuration of the image pickup unit 515 connected to the distal end of the arm unit 512 as a distal end unit is not particularly limited, and for example, the image pickup unit 515 is configured as a microscope that acquires an enlarged image of the image pickup target. In addition, the image pickup unit 515 may be configured to be detachable from the arm unit 512. With such a configuration, for example, the image pickup unit 515 according to usage application may be appropriately connected to the distal end of the arm unit 512 as a distal end unit. Note that, in the invention, although a description is given focusing on a case in which the image pickup unit 515 is applied as a distal end unit, the distal end unit connected to the distal end of the arm unit 512 is not necessarily limited to the image pickup unit 515.

In addition, a display apparatus 550 such as a monitor or a display is installed at a position facing the user 520. An image of a medical treatment region which is picked up by the image pickup unit 515 is displayed on a display screen of the display apparatus 550 as an electronic image. The user 520 performs various treatment while viewing an electronic image of the medical treatment region displayed on the display screen of the display apparatus 550.

With the above-described configuration, it is possible to perform surgery while picking up an image of a medical treatment region by the video microscope apparatus for surgery 510.

6. CONCLUSION

As described above, the imaging system according to the present embodiment includes a light source apparatus that irradiates a predetermined image pickup target with light including a component in at least a portion of a wavelength band of an excitation wavelength of a fluorescent material with respect to each of the plurality of types of fluorescent materials. Examples of the plurality of types of fluorescent materials include fluorescent materials (for example, ICG and the like) emitting fluorescence belonging to a near-infrared wavelength band and fluorescent materials (for example, 5ALA, laserphyrin, fluorescein, and the like) emitting fluorescence belonging to a visible light wavelength band. In addition, the imaging system according to the present embodiment includes an image pickup apparatus (for example, a camera head) which picks up an image acquired by a predetermined optical system unit such as an endoscope unit or a microscope unit. The image pickup apparatus includes a branching optical system (for example, color separation prisms 201a to 201c or the like) including a dichroic film which separates light belonging to a visible light wavelength band and light belonging to a near-infrared wavelength band. In addition, the image pickup apparatus includes a first image pickup element (for example, the image pickup element for picking up the near-infrared light image 1052) which is provided at the succeeding stage of the branching optical system and on which light belonging to a near-infrared wavelength band and separated by a dichroic film is imaged, and a second image pickup element (for example, the image pickup element for picking up the visible light image 1051) on which light belonging to a visible light wavelength band and separated by the dichroic film is imaged. Based on such a configuration, the imaging system according to the present embodiment picks up a fluorescent image of fluorescence belonging to a near-infrared wavelength band and emitted from ICG or the like on the first image pickup element side, and picks up a fluorescent image of fluorescence belonging to a visible light wavelength band and emitted from 5ALA, laserphyrin, fluorescein, or the like on the second image pickup element side.

With the above-described configuration, the imaging system according to the present embodiment can pick up a fluorescent image, corresponding to a fluorescent material to be used, in a more suitable mode even under a situation where a plurality of types of fluorescent materials is selectively used.

Further, as described above, in the image pickup apparatus applied to the imaging system according to the present embodiment, an IR cut filter is not provided at the front stage of the second image pickup element picking up an image of light belonging to a visible light wavelength band, and a short pass filter or a bandpass filter is provided instead. With such a configuration, it is possible to prevent the occurrence of a situation where fluorescence, belonging to a visible light wavelength band (particularly, a wavelength band on a long wavelength side), which is emitted from 5ALA or laserphyrin and is guided to the second image pickup element is limited by the IR cut filter when the fluorescence is imaged on the second image pickup element. That is, according to the imaging system of the present embodiment, since it is possible to more utilize performance of the second image pickup apparatus (particularly, the image pickup element) also in a case in which a fluorescent image of fluorescence belonging to a visible light wavelength band is picked up, it is possible to pick up a clearer fluorescent image.

The preferred embodiment (s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An imaging system including:

a light source apparatus which irradiates a predetermined image pickup target with light including a component in at least a portion of a wavelength band of an excitation wavelength of each of a plurality of types of fluorescent materials including a first fluorescent material emitting fluorescence belonging to a near-infrared wavelength band and a second fluorescent material emitting fluorescence belonging to a visible light wavelength band; and an image pickup apparatus which picks up an image acquired by a predetermined optical system unit, in which the image pickup apparatus includes a branching optical system that includes a dichroic film separating the light belonging to the visible light wavelength band and the light belonging to the near-infrared wavelength band from each other, a first image pickup element which is provided at a stage after the branching optical system and on which the light belonging to the near-infrared wavelength band which is separated by the dichroic film is imaged, and a second image pickup element which is provided at a stage after the branching optical system and on which at least a portion of the light belonging to the visible light wavelength band which is separated by the dichroic film is imaged, a fluorescent image of the fluorescence emitted from the first fluorescent material is picked up by the first image pickup element, and a fluorescent image of the fluorescence emitted from the second fluorescent material is picked up by the second image pickup element.

(2)

The imaging system according to (1), in which the image pickup apparatus includes a short pass filter which is disposed in a light path of the light separated by the dichroic film and imaged on the second image pickup element, and transmits light having a wavelength equal to or less than a wavelength corresponding to a boundary between the visible light wavelength band and the near-infrared wavelength band.

(3)

The imaging system according to (2), in which the image pickup apparatus includes a notch filter which is provided at a stage before the branching optical system and blocks light in at least a portion of a wavelength band of the excitation wavelength of the first fluorescent material, and a long pass filter which is disposed in a light path of the light separated by the dichroic film and imaged on the first image pickup element, and transmits light having a wavelength equal to or greater than the wavelength corresponding to the boundary.

(4)

The imaging system according to (2), in which the image pickup apparatus includes a bandpass filter which is disposed in a light path of the light separated by the dichroic film and imaged on the first image pickup element, transmits light in at least a portion of a wavelength band of the fluorescence emitted from the first fluorescent material, and blocks light in at least a portion of a wavelength band of the excitation wavelength of the first fluorescent material.

(5)

The imaging system according to (1), in which the branching optical system includes a second dichroic film which separates the light belonging to the visible light wavelength band which is separated by a first dichroic film serving as the dichroic film, into light belonging to a first wavelength band including at least a portion of a wavelength band of the fluorescence emitted from the second fluorescent material and light belonging to a second wavelength band different from the first wavelength band, on the second image pickup element, the light belonging to the first wavelength band which is separated by the second dichroic film is imaged among the light belonging to the visible light wavelength band which is separated by the first dichroic film, and the image pickup apparatus includes a third image pickup element on which the light belonging to the second wavelength band which is separated by the second dichroic film is imaged, among the light belonging to the visible light wavelength band which is separated by the first dichroic film a first bandpass filter which is disposed in a light path of the light which is separated by the first dichroic film and imaged on the first image pickup element, transmits light in at least a portion of a wavelength band of the fluorescence emitted from the first fluorescent material, and blocks light in at least a portion of a wavelength band of the excitation wavelength of the first fluorescent material, a second bandpass filter which is disposed in a light path of the light which is separated by the second dichroic film and imaged on the second image pickup element and transmits light in at least a portion of a wavelength band of the first wavelength band, and a third bandpass filter which is disposed in a light path of the light which is separated by the second dichroic film and imaged on the third image pickup element and transmits light in at least a portion of a wavelength band of the second wavelength band.

(6)

The imaging system according to (5), in which the first wavelength band is a wavelength band on a long wavelength side including a wavelength band of an R component in the visible light wavelength band, and the second wavelength band is a wavelength band on a short wavelength side including a wavelength band of a G component and a wavelength band of a B component in the visible light wavelength band.

(7)

The imaging system according to any one of (1) to (6), in which the light source apparatus emits first light which is continuously distributed in the visible light wavelength band and has a peak equal to or greater than a predetermined threshold value at a predetermined wavelength position, and second light which includes a component in at least a portion of a wavelength band of excitation wavelength of the first fluorescent material in the near-infrared wavelength band.

(8)

The imaging system according to (7), in which the light source apparatus includes a first light source unit which emits the first light having the peak at a plurality of wavelength positions, and a second light source unit which emits the second light, and the first light source unit is capable of controlling output of light corresponding to at least a wavelength position which is included in a wavelength band of fluorescence emitted from the second fluorescent material or which is positioned closer to the wavelength band among the plurality of wavelength positions.

(9)

The imaging system according to (8), in which the first light has the peak at respective wavelength positions corresponding to an R component, a G component, and a B component, and the first light source unit is capable of controlling output of at least light corresponding to the R component in the first light.

(10)

The imaging system according to (8) or (9), in which the first light source unit is a laser light source.

(11)

The imaging system according to any one of (1) to (10), further including an endoscope unit which includes a lens barrel to be inserted into a body cavity of an examination subject, as the optical system unit.

(12)

The imaging system according to any one of (1) to (10), including a microscope unit which acquires an enlarged image of the image pickup target, as the optical system unit.

REFERENCE SIGNS LIST 100 endoscopic surgery system
101 endoscope
103 lens barrel
105 camera head
1051 image pickup element for picking up visible light image
1052 image pickup element for picking up near-infrared light image
1053 FPGA
1054 optical system unit
1055 notch filter
143 light source apparatus
1431 visible light source
1433 near-infrared light source
201 branching optical system
203 dichroic film
205 first prism
207 second prism
211 short pass filter
213 long pass filter
215 bandpass filter

The invention claimed is:

1. An imaging system comprising:
a light source configured to emit light including a component in at least a first excitation wavelength band to excite a first fluorescence material emitting a first fluorescence belonging to a near-infrared wavelength band, and to emit light including a component in at least a second excitation wavelength band to excite a second fluorescence material emitting a second fluorescence belonging to a visible wavelength band;
a first image sensor configured to receive light including a component of the wavelength band of the first fluorescence and output a first imaging signal;
a second image sensor configured to receive light including a component of the wavelength band of the second fluorescence and output a second imaging signal;
an optical element configured to separate light including the first fluorescence in the near-infrared wavelength band into a first optical branch and light including the second fluorescence in the visible wavelength band into a second optical branch;
a first pass filter in the first optical branch configured to transmit light having a near-infrared wavelength band and block light having a wavelength equal to or less than a predetermined wavelength belonging the visible wavelength band; and
a second pass filter in the second optical branch to transmit light in the visible wavelength band that includes red light and block light in the visible wavelength band that includes green and blue light.

2. The imaging system according to claim 1, wherein the optical element includes a dichroic film configured to transmit light in the near-infrared wavelength band and reflect light in the visible wavelength band.

3. The imaging system according to claim 2, wherein the optical element includes a first prism and a second prism, wherein the dichroic film is between the first prism and the second prism.

4. The imaging system according to claim 3, wherein the first pass filter is a long pass filter.

5. The imaging system according to claim 4, wherein the predetermined wavelength is a wavelength corresponding to a boundary between the near-infrared wavelength band and the visible wavelength band.

6. The imaging system according to claim 5, further comprising: a notch filter before the dichroic film, the notch filter blocking light in at least a portion of the first excitation wavelength band of the first fluorescent material.

7. The imaging system according to claim 6, further comprising: wherein the second pass filter is a short pass filter that transmits light having a wavelength equal to or less than a wavelength corresponding to a boundary between the visible wavelength band and the near-infrared wavelength band.

8. An endoscope system comprising:
a light source configured to emit light including a component in at least a first excitation wavelength band to excite a first fluorescence material emitting a first fluorescence belonging to a near-infrared wavelength band, and to emit light including a component in at least a second excitation wavelength band to excite a second fluorescence material emitting a second fluorescence belonging to a visible wavelength band;
a camera head including:
a first image sensor configured to receive light including a component of the wavelength band of the first fluorescence and output a first imaging signal,
a second image sensor configured to receive light including a component of the wavelength band of the second fluorescence and output a second imaging signal,
an optical element configured to separate light, received via an endoscope scope, including the first fluorescence in the near-infrared wavelength band into a first optical branch and light including the second fluorescence in the visible wavelength band into a second optical branch,
a first pass filter in the first optical branch configured to transmit light having a near-infrared wavelength band and block light having a wavelength equal to or less than a predetermined wavelength belonging the visible wavelength band, and
a second pass filter in the second optical branch to transmit light in the visible wavelength band that includes red light and block light in the visible wavelength band that includes green and blue light; and
camera control circuitry configured to obtain a first fluorescence image signal generated based on a signal from the first fluorescence captured by the first image sensor or a second fluorescence image signal generated based on a signal from the second fluorescence captured by the second image sensor.

9. The endoscope system according to claim 8, wherein the optical element includes a dichroic film configured to transmit light in the near-infrared wavelength band and reflect light in the visible wavelength band.

10. The endoscope system according to claim 9, wherein the optical element includes a first prism and a second prism, wherein the dichroic film is between the first prism and the second prism.

11. The endoscope system according to claim 10, wherein the first pass filter is a long pass filter.

12. The endoscope system according to claim 11, wherein the predetermined wavelength is a wavelength corresponding to a boundary between the near-infrared wavelength band and the visible wavelength band.

13. The endoscope system according to claim 12, further comprising: a notch filter before the dichroic film, the notch filter blocking light in at least a portion of the first excitation wavelength band of the first fluorescent material.

14. The endoscope system according to claim 13, wherein the second pass filter is a short pass that transmits light having a wavelength equal to or less than a wavelength corresponding to a boundary between the visible wavelength band and the near-infrared wavelength band.

15. The endoscope system according to claim 8, the camera control circuitry is further configured to superimpose at least one of the first fluorescence image signal or the second fluorescence image signal onto a visible light image signal.

16. An endoscope device comprising:
a camera head including:
a first image sensor configured to receive light including a component of a wavelength band of a first fluorescence and output a first imaging signal, the first fluorescence, belonging to a near-infrared wavelength band, being emitted from a first fluorescence material by first excitation light,
a second image sensor configured to receive light including a component of a wavelength band of a second fluorescence and output a second imaging signal, the second fluorescence, belonging to a visible wavelength band, being emitted from a second fluorescence material by second excitation light,
an optical element configured to separate light, via a scope, including the first fluorescence in the near-infrared wavelength band into a first optical branch and light including the second fluorescence in the visible wavelength band into a second optical branch,
a first pass filter in the first optical branch configured to transmit light having a near-infrared wavelength band and block light having a wavelength equal to or less than a predetermined wavelength belonging the visible wavelength band, and
a second pass filter in the second optical branch to transmit light in the visible wavelength band that includes red light and block light in the visible wavelength band that includes green and blue light.

17. The endoscope device according to claim 16, wherein the optical element includes a dichroic film configured to transmit light in the near-infrared wavelength band and reflect light in the visible wavelength band.

18. The endoscope device according to claim 17, wherein the optical element includes a first prism and a second prism, wherein the dichroic film between the first prism and the second prism.

19. The endoscope device according to claim 18, wherein the first pass filter is a long pass filter.

20. The endoscope device according to claim 19, wherein the predetermined wavelength is a wavelength corresponding to a boundary between the near-infrared wavelength band and the visible wavelength band.

* * * * *